(12) United States Patent
Hasegawa et al.

(10) Patent No.: US 6,482,441 B1
(45) Date of Patent: Nov. 19, 2002

(54) COATED POWDER HAVING SUPER-DISPERSIBILITY AND COSMETIC CONTAINING THE SAME

(75) Inventors: Yukio Hasegawa, Koshigaya (JP); Ryo Ohara, Urawa (JP)

(73) Assignee: Miyoshi Kasei, Inc., Saitama (JP)

( * ) Notice: Subject to any disclaimer, the term of this patent is extended or adjusted under 35 U.S.C. 154(b) by 0 days.

(21) Appl. No.: 09/609,698

(22) Filed: Jul. 6, 2000

(30) Foreign Application Priority Data

Jul. 8, 1999 (JP) ............................................. 11-194570
Mar. 16, 2000 (JP) ........................................ 2000-073261

(51) Int. Cl.⁷ ................................................. A61K 9/50
(52) U.S. Cl. ........................................................ 424/490
(58) Field of Search .......................................... 424/490

(56) References Cited

FOREIGN PATENT DOCUMENTS

| JP | 62087237 A | 4/1987 | |
| JP | 05-339518 | 12/1993 | |
| JP | 07062263 | * 3/1995 | |
| JP | 07-196946 | 8/1995 | |
| JP | 09295917 | * 11/1997 | |
| JP | 11-029719 | 2/1999 | |
| JP | 11-080588 | 3/1999 | |
| JP | 11217314 | * 8/1999 | |

* cited by examiner

*Primary Examiner*—Alton Pryor
(74) *Attorney, Agent, or Firm*—Armstrong Westerman & Hattori, LLP

(57) ABSTRACT

In the present invention, the surface-treated powder (the coated powder) can be used as a powder for cosmetics. With the coated powder for cosmetics, dispersibility of the powder and the functions proper to the powder, such as adhesion to the skin, aesthetic feel (using touch), covering power, coloring power, UV or IR light shielding performance, optical characteristics (properties) and the like, may be improved significantly. In particular, the coated powder is superior in affinity to oleophilic liquids, dispersibility, and dispersion stability and may be applied to cosmetics and powders in the fields other than cosmetics.

8 Claims, No Drawings

COATED POWDER HAVING SUPER-DISPERSIBILITY AND COSMETIC CONTAINING THE SAME

BACKGROUND OF THE INVENTION

1. Field of the Invention

The present invention relates to a novel coated powder exhibiting super-dispersibility and, more particularly, it relates to surface-treated powder comprising a powder usable for cosmetics, and coating layers of surface treating agents containing a layer A that is a solid at room temperature and a layer B that is a liquid at room temperature, each formed on at least a portion of the powder particle surface, and to a cosmetic containing the surface-treated powder. More particularly, it relates to a surface-treated powder having coating layers of surface treating-agents, in which the coating layer of a surface treating agent of layer A as a first layer, and the coating layer of a surface treating agent of layer B as a second layer, are each formed on at least a portion of the powder particle surface. Layer A is a coating layer of a surface treating agent that is a solid at room temperature and contains at least one compound selected from the compounds contained in reactive organo polysiloxane, polyolefin, hydrogenated lecithin, including its salt forms, N-acylamino acid, including its salt forms, fatty acid, including its salt forms, and dextrin fatty acid esters. Layer B is a coating layer of a surface treating agent that is a liquid at room temperature, and contains at least one compound selected from the compounds contained in organo polysiloxane modified at its sole terminal end with a functional group, alkylsilane modified at its sole terminal end with a functional group, and branched fatty acid, and to a cosmetic containing the surface-treated powder.

The surface-treated powder of the present invention exhibits super-dispersibility, so that, when the surface-treated powder of the present invention is mixed into a formula (composition for cosmetics) not containing an oleophilic liquid, that is a system containing only powders, it exhibits superior dispersibility. Moreover, if the surface-treated powder of the present invention is mixed into a system containing oleophilic liquid; the surface-treated powder is superior in affinity to the liquid and hence superior in dispersibility and dispersion stability. Moreover, the surface-treated powder of the present invention drastically improves the functions of the powder base that vary according to the dispersed state, for example, adhesion to the skin, aesthetic feeling (using touch), covering power, coloring power, shielding power against UV or IR rays and optical characteristics (properties), as compared to those of conventional surface-treated powders.

Therefore, the cosmetic containing the surface-treated powder according to the present invention can be appreciably improved as to the functions as cosmetics.

The powder obtained in this manner can be applied not only to cosmetics, but also to surface-treated powders that finds application in a variety of other technical fields such as additives for plastics, inks, paints, toners (magnetic powders) and the like.

2. Description of the Related Art

Powders mixed into cosmetics are oleophilized in order to eliminate the powdery feeling, reduce physical stimuli to the skin, improve adhesiveness to the skin, improve dispersibility in an oleophilic liquid and improve wear on the skin. These oleophilized powders are usually mixed with an oily component and used in formulations. As the powder materials approaches its primary particles when mixed or dispersed, the powder material exhibits its optimum potential of its functional properties. In order to reach this optimum point of functionality, which relates to adhesion, aesthetic feeling (using touch), covering power, coloring power, optical properties, absorption and/or scattering of UV and IR rays to the fullest extent, excellent affinity as well as excellent dispersibility of the powder to an oily agent is necessary, because poor affinity with the oily agent leads to flocculation to render it impossible to display its maximum potential characteristics.

In order to solve this problem, it has been proposed to have the surface of the powder material coated with an oleophilic material. Although the adhesion to the skin of the powder material, as well as its rough feeling is improved by this method to some extent, the powder material becomes flocculated by the surface treating agent itself such that dispersibility does not reach its optimum state. Furthermore, in order to disperse the powder material into an oleophilic liquid, it is necessary to assort a large quantity of surfactants to improve its affinity into the oil and to achieve dispersion stability.

On the other hand, powdered organic materials, exemplified by polyethylene powder, nylon powder, polystyrene powder and methyl methacrylate powder, etc. is itself oleophilic such that it is in many cases better in dispersibility into an oleophilic liquid than the inorganic material. However, organic material suffers from drawbacks such as extremely poor adhesion to the skin and a tendency to be statically charged and therefore become flocculated, which lowers its dispersibility, etc., significantly. In order to improve upon this, a variety of surface treating methods have so far been proposed.

This kind of surface treating method routinely coats the material with organic surface treating agents, such as silicones, organic silanes, N-acylamino acids, fatty acids, hydrogenated lecithin, fluorine compounds, polyethylene, ester-based oily agents and the like. Specifically, there have been proposed a surface treating method with methyl hydrogen polysiloxane (Refer to Japanese Patent Kokai Publications JP-A-60-163973, JP-A-61-127767, JP-A-61-190567, JP-A-61-215216, JP-A-63-30407, JP-A-63-139015, JP-A-63-165461, JP-A-1-110540, JP-A-3-163172 and JP-A-4-246474, and Japanese Patent Kokoku Publications JP-B-1-54379, JP-B-1-54380 and JP-B-1-54381.), a surface treating method with various silane coupling agents (Refer to Japanese Patent Kokai Publications JP-A-62-177070, JP-A-2-218603 and JP-A-4-193816.), a method for surface-treating with other silicones (Refer to Japanese Patent Kokai Publications JP-A-4-202109, JP-A-4-202110, JP-A-4-202111, JP-A-5-86368, JP-A-7-206637, JP-A-7-206638, JP-A-7-207187 and JP-A-11-80588.), and a method for surface-treating with alkylsilane (Refer to Japanese Patent Kokai Publications JP-A-61-204112, JP-A-64-90111, JP-A-8-92052, JP-A-8-104606 and JP-A-8-104612.).

Further, a method for surface-treating with N-acylamino acids has been proposed in, for example Japanese Patent Kokai Publications JP-A-61-737775, JP-A-61-69709, JP-A-3-200879, JP-A-5-186706, JP-A-9-328413, JP-A-10-226626 and the like, whilst a method for coating with fatty acids is proposed in Japanese Patent Kokai Publications JP-A-60-69011 and the like, and a method for surface-treating with hydrogenated lecithin is proposed in Japanese Patent Kokai Publications JP-A-60-184571, JP-A-60-190705 and the like.

There are also known methods of enhancing the function of the powdered base material by coating the powder material with plural surface treating agents in combination. Specifically, powder material coated with methyl hydrogen polysiloxane and trimethyl siloxy silicic acid (Refer to Japanese Patent Kokai Publications JP-A-7-62263 and the like.), powder material coated with a titanium coupling agent or an alkylsilane compound, and an oleophilic material not having a functional group (Refer to Japanese Patent Kokai Publications JP-A-11-29719 and the like.) and powder material coated with methyl hydrogen polysiloxane, trimethyl siloxysilicic acid and cross-linked methyl polysiloxane in combination (Refer to Japanese Patent Kokai Publications JP-A-11-80588 and the like.).

SUMMARY OF THE INVENTION

1. Problem to be Solved by the Invention

However, there are as yet left problems to be solved in the aforementioned conventional surface treating methods.

First, the aforementioned surface treating agents are mostly solid at ambient room temperature on the surface of the powder particle material, so that, when the surface treating agent is applied to the powder particle material, smooth feeling and adhesion to the skin is improved to some extent, however, the particles tend to flocculate during the coating process. This results in poor dispersion when mixing the powder material, in particular to low affinity oleophilic liquids, and insufficient dispersibility and dispersion stability. For example, titanium dioxide or iron oxide contained in make-up cosmetics, etc., termed as "pigment grade", with a particle size of 0.1 to 0.3 μm, is poor in dispersibility in an oily agent, and therefore does not exhibit optimum covering power or coloring power. In many cases, evaluation only of the covering power or coloring power demonstrates that the powder material not surface-treated is better than the surface-treated material.

When the steps of pulverization and dispersion are repeated, problems arises from the point of process complexity and high cost. If a surfactant is assorted as a dispersion stabilizer, there are undesirably imposed constraints on the development of formulation variety and amount that can be used. In addition, the surface treating agent is poor in affinity to an oleophilic liquid and insufficient in dispersibility such that a difference undesirably tends to be produced, between the application color and appearance color.

If, in an attempt to improve smoothness and adhesion to the skin of an extender, such as mica or sericite, the amount of the surface treating agent is increased, flocculation of particles progresses further. Furthermore increasing the amount of solid surface treatment increases the coating thickness, thereby giving the particle a heavy feeling and a loss of smoothness.

In the case of pigmentary grade titanium dioxide or iron oxide assorted into e.g., nail lacquer, color demarcation or separation tends to be produced with time due to poor dispersion stability into the organic solvent. There is a need of a surface-coated powdered material effective to prevent this. At the present moment organic modified clay minerals, which give an increase in thixotropy, are used in order to accommodate for the surface-coated powder material to prevent precipitation and color separation.

In order to improve the properties of adhesion on to the skin, water proofness, achieve high solid content O/W type emulsions or creams with low oily phase content, increase solid content into oleophilic components for pre-dispersion pastes that are used to improve the handling of fine particulate powders, and achieve high stability, of fine titanium dioxide, zinc oxide, cerium oxide, zirconium oxide or silicon oxide, used for shielding UV or IR light, conventional coatings are not sufficient.

On the other hand, the present inventors have reported that, if a powdered material is coated with a straight-chained dimethyl polysiloxane modified at the terminal end with a trialkoxy group, there is obtained a powder material which is free from flocculation of the particles of the powder material, has a smooth feeling, good adhesion to the skin, and superior spreading properties for colored pigments (Refer to Japanese Patent Kokai Publications JP-A-5-339518 and JP-A-7-196946.). With this surface treating agent, a liquid coating layer is formed at room temperature even after coating thereof on the particle surface, so that it has excellent adhesion to the skin, a lubricious feeling (slipperiness), and excellent affinity or dispersibility in an oleophilic liquid compared to conventional surface treated particulates. However, when one tries to further increase these functions, dispersion in the oleophilic liquid is not necessarily improved even when the coating quantity is increased. For this reason a coated powdered material is desired, which can further improve these functions, such as adhesion to the skin, aesthetic feeling (using touch), covering power, coloring power, UV or IR light shielding power and other optical properties, and is superior in affinity and dispersibility in the oleophilic liquid.

In addition, formulations for cosmetic are recently designed to exploit the optical performance of the powder material. Optical characteristics of powder materials are determined depending on the particle shape, particle size distribution, and refractive index of the powder material. These inherent optical properties of the material cannot be displayed readily if the material is poor in dispersibility, thus necessitating excess amounts of the material in the formulation. This reinforces the demand for a powder material having superior dispersibility.

It is an object of the present invention to provide a coated powdered material obtained on surface-treating a powdered material for cosmetic, with which dispersibility of the powdered material and various functions proper to the powdered material, such as adhesion to the skin, aesthetic feeling (using touch), covering and coloring power, UV and IR light shielding power and optical properties, maybe improved further, and which is superior in affinity to oleophilic liquids, in dispersibility and in dispersion stability.

Based on the following concept and experimentation, the present inventors have completed a surface-treated powdered material which, by applying two layers of surface treating agents thereon, displays excellent (super)-dispersibility, in particular superior dispersibility in oleophilic liquids. That is, the present inventors conducted perseverant searches into a stable surface treating agent which displays strong water repellency and oleophilicity over an extended period of time as a first coating layer (layer A) formed on the outermost surface of the particles of the powdered material, and which gives a homogeneous, extremely strong surface coated layer; and into a surface treating agent which as a second coating layer (layer B) is able to protect the first coating layer against mechanical impacts, exhibits high affinity to oleophilic liquids, and which thereby gives superior dispersibility and dispersion stability. Thus, we have found that, by coating the powdered material (substrate) with a solid surface treating agent, as a first layer, and by coating the substrate, having the first layer, with a liquid surface treating agent as a second layer, a surface-treated powdered material can be produced which displays hitherto unprecedented high performance.

That is, the present inventors conducted perseverant searches towards accomplishing the above object, and found that, if at least two layers, preferably a layer A, on the powder particle surface and a layer B on the layer A, on at least a portion of the surface of the powder usable for cosmetics, specifically on the entire powder surface or on a portion thereof, to form a layer coated with a surface treating agent that is a liquid at room temperature, with layer A being a coating layer of a surface treating agent that is a solid at room temperature, containing at least one compound selected from the compounds contained in a reactive organo polysiloxane, a polyolefin, a hydrogenated lecithin, including its salt form such as a metal salt, a N-acylamino acid, including its salt form such as a metal salt, a fatty acid, including its salt form such as a metal salt, and a dextrin fatty acid ester, and with layer B being a coating layer of a surface treating agent that is a liquid at room temperature, containing at least one compound selected from the compounds contained in an organo polysiloxane modified at its sole terminal end with a functional group, an alkylsilane modified at its sole terminal end with a functional group and a branched fatty acid, the resulting novel coated powder is extremely effective as a powder achieving the above objective, with the powder being particularly excellent in affinity to and hence in dispersibility in an oleophilic liquid. This finding has led to the completion of the present invention.

Thus, the present invention resides in a surface-treated powder comprising a powder usable for cosmetics, and coating layers of surface treating agents of a layer A and a layer B, each formed on at least a portion of the powder particle surface, wherein the layer A is a coating layer of a surface treating agent that is a solid at room temperature, the coating layer containing at least one compound selected from the compounds contained in the group consisting of a reactive organo polysiloxane, a polyolefin, a hydrogenated lecithin, including its salt forms, an N-acylamino acid, including its salt forms, a fatty acid, including its salt forms, and a dextrin fatty acid ester; and wherein the layer B is a coating layer of a surface treating agent that is a liquid at room temperature, the coating layer containing at least one compound selected from the compounds contained in the group consisting of an organo polysiloxane modified at its sole terminal end with a functional group, an alkylsilane modified at its sole terminal end with a functional group, and a branched fatty acid.

The present invention also is directed to a cosmetic containing the surface-treated powder.

On the powder thus treated, the layer A and the layer B are solid and liquid at room temperature, respectively.

EMBODIMENTS OF THE INVENTION

As a particularly preferred embodiment of the present invention, the surface-treated powdered material (powder) sequentially coated with a layer A and with a layer B in this order is mainly explained as embodying the present invention. The present invention is, however, intended to cover the following modifications as explained, including the preferred embodiment without being limited thereto.

The powdered material (substrate) is such a powdered material which can be used for cosmetics, and which has an average particle size preferably of about 500 to 0.01 $\mu$m and more preferably of about 100 to 0.01 $\mu$m.

There is no particular limitation to the powdered material (substrate) to be surface-treated for use in the present invention, provided the powdered material (substrate) is one routinely used for cosmetics. In addition however, the powdered material (substrate) can be used not only for cosmetic but also for surface-treated powders used in a wide range of fields of application such as additives for plastics, inks, paints or toners (magnetic powders). The average particle size is preferably tens of microns ($\mu$m) to about 0.01 micron ($\mu$m).

As for the methods for measuring the particle size, the laser diffraction method or a precipitation method is used for particles with a particle size of 0.1 $\mu$m or greater, whereas a photon correlation method or an electron microscope is used for particles with a particle size of 0.1 $\mu$m or less.

For example, inorganic powdered materials may be enumerated by mica, sericite, talc, kaolin, synthesized mica, calcium carbonate, magnesium carbonate, magnesium silicate, aluminum silicate, calcium phosphate, silicic anhydride, alumina, magnesium oxide, aluminum hydroxide, barium sulfate, magnesium aluminosilicate, magnesium aluminometasilicate, boron nitride, zeolite, hydroxy apatite, ceramic powders and the like, as an extender.

White-colored pigments may be enumerated by titanium dioxide, zinc oxide and cerium oxide, while colored pigments may be enumerated by red iron oxide, yellow iron oxide, black iron oxide, chromium oxide, chromium hydroxide, Prussian blue, ultramarine blue, carbon black, low order titanium oxide, mango violet and the like. Pearl pigments may be enumerated by bismuth oxychloride, mica titanium, fish scale foil and the like, while fine particulate powders may be enumerated by fine particulate titanium dioxide, fine particulate zinc oxide, fine particulate iron oxide, fine particulate cerium oxide and the like. Finally, some other powdered materials may be enumerated by aluminum powders, stainless steel powders and the like. These powders may be used singly or as a mixture.

These powdered materials may be compounded to form composite pigments if needed. For example, powdered materials comprising inorganic colored pigments, such as red iron oxide, coated with a silicic anhydride, powdered materials comprising of an extender, coated with a fine particulate white-colored pigments, or the like may be used.

Organic powdered materials may be enumerated by polyamide, polyester, polyethylene, polypropylene, polystyrene, polyurethane, vinyl resin, urea resin, phenolic resin, fluorine resin, silicon resin, acrylic acid resin, melamine resin, epoxy resin, polycarbonate resin, divinylbenzene-styrene copolymer, copolymers composed of two or more of the above monomers, celluloid, acetyl cellulose, cellulose, polysaccharides, protein, organic tar dyes and the like.

According to the present invention, the surface of the surface-treated powdered material (powder particle) is covered at least partially with layer A and layer B. Typically, layer A is applied to the surface of the particulate powder in contact therewith, and layer B is applied to layer A in contact therewith. A double coating layer comprising of layer A and layer B are desirably applied to the entire surface of the particulate powder, since thereby the meritorious effect of the present invention can be displayed sufficiently. However, only one of the layers A and B may be present on a certain portion of the powder particle surface, whereas neither layer A nor layer B may be present on an extremely small portion of the surface of the particulate powders, although on extremely rare occasions.

Another distinct layer may also be provided between layers A and B or between layer A and the particle surface of the powdered material (substrate) to the extent without impairing the object of the present invention.

The following explanation is made mainly with respect to powdered materials in which layer A is applied in contact with the surface of the powdered material and layer B is applied in contact with layer A. However, the present invention is not limited to this particular embodiment, as described above.

Layer A is a coating layer of the surface treating agent applied in contact with the surface of the particulate powder and which is a solid at room temperature. On the other hand, layer B is a coating layer of the surface treating agent applied in contact with layer A applied in contact with the surface of the particulate powder. Layer B is a liquid at room temperature. What the inventors mean by the coating layer of the surface treating agent being a solid at room temperature, is that the surface treating agent when coated on the surface of the particulate powder is and remains as a solid at room temperature. Suffice to say, that the coating layer of the surface treating agent is a liquid at room temperature, means that the coating layer of the surface treating agent as coated thereon is and remains as a liquid at room temperature. Therefore, it suffices if layer A and layer B is solid and liquid, respectively, at room temperature as applied to the surface of the particulate powder. It is noted that, prior to coating on the surface of the particles, the surface treating agents in question may be liquid or solid, however, the surface treating agents are needed in the aforementioned state when the surface treating agent is once applied.

Moreover, the surface treating agent is solid or liquid at room temperature means directly that the surface treating agent is solid or liquid at room temperature, furthermore, the liquid state particularly can be identified as possessing a "lubricious feel".

It is noted that certain surface treating agents exhibit a lubricious feel even if the agent is solid at room temperature. For example, N-lauroyl-L-lysine, boron nitride, silicone resin powders, silicone rubber powders, polytetrafluoroethylene powders and the like are of the lamellar or spherical particle shape and present extremely smooth feeling because of the properties of the compounds in question, so that a powdered material coated with these compounds sometimes present a lubricious feel. However, the meritorious effect proper to the present invention cannot be achieved with these compounds (when used for the layer B).

Layer A is a coating layer of a surface treating agent that is a solid at room temperature, and which contains at least one compound selected from the compounds contained in the group consisting of a reactive organo polysiloxane, polyolefin, such as polyethylene, polypropylene, etc., hydrogenated lecithin, including salts thereof, N-acylamino acid, including salts thereof, and dextrin fatty acid ester. Layer B is a coating layer of a surface treating agent that is a liquid at room temperature, which contains at least one compound selected from the compounds in the group consisting of an organo polysiloxane modified at a sole terminal end with a functional group, an alkylsilane modified at a sole terminal end with a functional group, and a branched fatty acid.

The coating layers A and B formed on the particle surface of the powder material according to the present invention may be construed to be the coating layers of the surface treating agents of the layers A and B in the meaning of the present invention, provided that the aforementioned ingredients used as the layers A and B of the present invention are affixed onto the powdered material.

(Reactive Organo Polysiloxane)

Among the reactive organo polysiloxanes, there are preferably included, organo hydrogen polysiloxane, polyalkoxy organo polysiloxane, triorgano siloxy silicic acid, organopolysiloxane modified at both terminal ends with trialkoxy groups, and the like.

As the reactive organo polysiloxanes used in accordance with the present invention, straight-chained or cyclic reactive organo polysiloxanes, represented by any of the following general formula (1) to (6), are particularly preferred. In these general formulas (1) to (6), plural $R^1$s, that is $R^1$s present not only in one of the general formulas but present in the general formulas (1) to (6) in their entirety, are independent from one another and respectively denote any one of lower alkyl groups with one to four carbon atoms, plural $R^2$s are similarly totally independent from one another and denote any one of hydrogen atoms, hydroxyl groups, and lower alkyl groups with one to four carbon atoms, n denotes an integer not less than two and m denotes zero or an integer, with n+m denoting an integer from 2 to 10000.

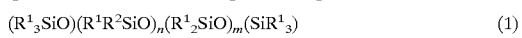

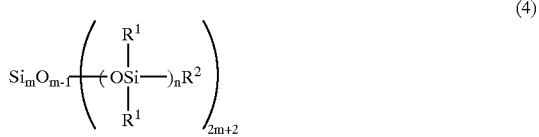

The compound represented by the general formula (1) with n equal to 0 or 1 is poor in reactivity on the surface of the particulate powders and presents a lubricious smooth feeling without assuming a three-dimensional meshed structure. This compound, however, is not desirable, since it fails to take part in rendering the powdered material hydrophobic or oleophilic.

It is more preferred that the compound of organo hydrogen polysiloxane, represented by the general formula (2), has n that is an integer of 3 to 7.

It is more preferred that the compound of organo hydrogen polysiloxane, represented by the general formula (3), has n that is an integer greater or equal to 2 and n+m is an integer of 3 to 7. The aforementioned cyclic hydrogen polysiloxane is ring-opened on the surface of the particulate powders to assume a three-dimensional meshed structure.

It is more preferred that the compound of polyalkoxy organo polysiloxane, represented by the general formula (4), has m that is an integer of 1 to 100 and the value of n/m is greater than or equal to 0.5.

It is sufficient if the reactive organo polysiloxane represented by the above general formulae (1) to (4) may undergo three-dimensional cross-linking reaction to form a resin, that is to be solidified, irrespective of whether or not the reactive organo polysiloxane is cyclic or straight-chained, as described above. The viscosity as measured at 25° C. is preferably on the order of 0.5 to 500 cs, more preferably on the order of 0.5 to 100 cs and further more preferably on the order of 1 to 50 cs. If the viscosity is less than 0.5 cs, the reaction is extremely quick so that particulate powders tend to become flocculated. The coating layer formed on the particle surface also becomes extremely vulnerable against shock and tends to peel off. If the viscosity exceeds 500 cs, the oil extends poorly, such that it is difficult to apply the reactive organo polysiloxane uniformly on the surface of the particulate powders. Such a surface treating agent may be exemplified by "KF-99" and "KF-9901" manufactured by SHIN-ETSU CHEMICAL CO. LTD., "SH-1107" manufactured by DOW CORNING TORAY SILICONE CO. LTD., "TSF484" and "TSF483" manufactured by TOSHIBA SILICONE CO. LTD., "FZ3704" and "AZ6200" manufactured by NIPPON UNICAR CO. LTD., and the like.

The compound having the following general formula (5) is triorgano siloxysilicic acid.

$$(R^1{}_3SiO_{1/2})_n(SiO_2)_m \quad (5)$$

wherein more preferably m and n are integers, m+n is an integer from 2 to 100 and a ratio n/m is a value equal to or less than 1.0.

If the ratio n/m exceeds 1.0, the coating layer on the surface of the particulate powders undesirably is not a hard solid coating layer but becomes an oily smooth coating layer. This oily coating layer is not desirable, since strong hydrophobicity or oleophilicity can not be achieved.

If trimethylsiloxysilicic acid is used in the present invention, agents yielded on replacing the sodium of water glass with a trimethylsilyl group and dissolving this in a solvent, in which the hardness of the hardened coating layer is controlled by an M/Q ratio corresponding to n/m in the above general formula (5) are extensively marketed and advantageously employed. For example, "KF-7312F", "KF-7312J", "KF-7312K", "KF-9001", "KF-9002", "X-21-5249" and "X-21-5250", manufactured by SHIN-ETSU CHEMICAL CO. LTD., "DC593", "BY-11-015", "BY-11-018" and "BY-11-022" manufactured by DOW CORNING TORAY SILICONE CO. LTD., and "TSF4600" manufactured by TOSHIBA SILICONE CO. LTD., etc.

The compound having the following general formula (6) is an organo polysiloxane modified at both terminal ends with functional groups and includes organo polysiloxane modified at both terminal ends with trialkoxy groups:

$$(R^2{}_3SiO)(R^1{}_2SiO)_n(SiR^2{}_3) \quad (6)$$

The above compound where n in the above general formula denotes an integer from 1 to 100 is more desirable.

As the organo polysiloxane modified at both terminal ends with functional groups, is employed in the present invention, those having a straight chain or a branched chain of T-shape and having siloxane repetition units of 1 to 100 are preferably used. If the value of n exceeds 100, reactivity with the surface of the particulate powders is lowered, while the as-reacted coating layer becomes a semi-solid (gelated) to liquid state giving a distorted feeling to render it difficult to achieve desirable effects proper to the present invention. The surface treating agent that can be purchased and employed readily includes, for example, "X-24-9817" and "X-24-9221" manufactured by SHIN-ETSU CHEMICAL CO. LTD., etc.

(Polyolefin)

As examples of polyolefins, such as polyethylene, polypropylene and the like, there is preferably a polyolefin resin having at least one carboxylic group (see, for example, Japanese Patent Kokai Publication JP-A-63-179972 proposed by the present inventors.). For example, low molecular weight polyethylene having a molecular weight of 500 to 20000 and a melting point not lower than 40° C., oxidized polyethylene, obtained on oxidizing polypropylene, polyethylene maleate, oxidized polypropylene and the like, these being marketed products, may be used.

(Hydrogenated Lecithin)

The hydrogenated lecithin, including its salt forms, is a glyceride containing phosphoric acid groups, and which is yielded on hydrogenating natural lecithin extracted from egg yolk, soybean, corn, coleseed (rapeseed) or the like and synthetic lecithin, and has an iodine value of preferably 30 or less and more preferably 15 or less. The hydrogenated lecithin in the salt form is preferably a salt of metals, such as Al, Mg, Ca, Zn, Zr and Ti, of a water insoluble hydrogenated lecithin. The hydrogenated lecithin (including its salt form) having a melting point of 50° C. or higher, is particularly desirable (See, for example, Japanese Patent Kokai Publications JP-A-60-184571 and JP-A-60-190705 and Japanese Patent Kokoku Publication JP-B-4-58443, proposed by the present inventors.). Conveniently, marketed "hydrogenated egg yolk oil No.5" manufactured by ASAHI CHEMICAL INDUSTRY CO. LTD., and similarly marketed hydrogenated soybean phospholipid ("BASIS LS-60 HR") manufactured by NISSHIN OIL MILLS, LTD., may be purchased and used.

(N-acylamino Acid)

N-acylamino acid is an amino acid having an acylated amino and/or imino group. The amino acid making up the N-acylamino acid may be a single amino acid or a mixture of plural or many different amino acids. If L-, D- or DL isomers exist for amino acid(s) making up the N-acylamino acid; any suitable one(s) of these isomers maybe used singly or in combination. The naturally existing L-isomer is more preferred.

The amino acids may be enumerated by glycine, alanine, β-alanine, valine, leucine, isoleucine, phenylalanine, proline, threonine, serine, arginine, histidine, lysin, aspartic acid, glutamic acid, tyrosine, methionine, cystine, cystein and the like.

The fatty acids making up the N-acyl derivative may preferably be exemplified by saturated or unsaturated fatty acids with 1 to 23 carbon atoms and fatty acids with 1 to 23 carbon atoms having a saturated or unsaturated alicyclic structure. For example, N-acylated glycine, n-acylated-N-methyl-β-alanine, N-acylated glutamic acid and the salts thereof may be used (see Japanese Patent Kokai Publication JP-A-61-73775 and Japanese patent Kokoku Publication JP-B-1-50202 proposed by the present inventors).

The constituent fatty acids in the N-acylamino acid are preferably long-chain fatty acids, such as caprylic acid, capric acid, lauric acid, myristic acid, isomyristic acid, palmitic acid, isopalmitic acid, stearic acid, isostearic acid, arachic acid, undecylenic acid, oleic acid, myristoleic acid, elaidic acid, linolic acid, linolenic acid, arachidonic acid, coconut oil fatty acid, beef fallow (fat) fatty acid, resin acid (abietic acid) and the like.

N-acylamino aid may be used in the free from or in the salt form(s). The salt form may be enumerated by salts of metals, such as Na, K, Ba, Zn, Ca, Mg, Fe, Zr, Co, Al, Ti and the like, ammonium salts, and a variety of alkanol amines, such as monoethanolamine, diethanolamine, triethanolamine, 2-amino-2-methyl-propanol, 2-amino-2-methyl-1, 3-propanediol, triisopropanolamine and the like.

Conveniently, commercially available products may be purchased and used. For example, N-acylated with coconut oil fatty acid or N-lauroyl-β-alanine (manufactured by KAWAKEN FINE CHEMICAL Co. LTD.), its Ca or Al salts, myristoyl silk amino acid and its Al salt, manufactured by PHYTOCOS INC., FRANCE, and N-lauroyl-L-lysine and N-stearoyl-L-glutamic acid, manufactured by AJINO-MOTO CO., INC., are preferred.

The N-acylating method may be any of known methods, such as those shown in Japanese Patent Kokai Publication JP-A-6-25627 and Japanese Patent Kohyou Publication JP-A-7-502010. For example, N-acylamino acid, obtained on N-acylating amino acids, obtained in turn on total hydrolysis of proteins derived from animals, such as silk, pearl and the like, or derived from plants, such as wheat, soybean and the like, using e.g., long-chain fatty acids, and further in the salt form on forming corresponding salts, where required, may be used as appropriate. As the amino acids used for preparing the N-acyl forms, at least 14 amino acids, namely glycine, L-alanine, L-valine, L-leucine, L-isoleucine, L-phenylalanine, L-proline, L-threonine, L-serine, L-arginine, L-histidine, L-lysine, L-aspartic acid and L-glutamic acid, are preferably contained. N-acyl forms of L-tyrosine, L-methionine, L-cystine, L-cystein and/or the like, may also be contained.

(Fatty Acid)

As fatty acids used in the present invention, those explained in connection with the fatty acids constituting the aforementioned N-acylamino acids, including its salt forms thereof, maybe used. As for the salt forms, those explained in connection with the n-acylamino acid in the salt form hold true unchanged. In particular, straight-chained saturated fatty acids, with 12 to 26 carbon atoms, such as fatty acids, including lauric acid, myristic acid, palmitic acid, stearic acid, behenic acid, lignoceric acid and cerotic acid, or the salts of metals, such as Ca, Mg, Zn, Zr, Al, Ti and the like thereof, are preferred (see, for example, Japanese Patent Kokai Publication JP-A-60-69011 proposed by the present inventors). In particular, the fatty acids that melt at 40° C. or higher are preferred.

If the number of carbon atoms is less than 12, the problem of stimuli to the skin tends to be raised. On the other hand, if the number of carbon atoms is more than 26, reactivity is lowered to render it difficult to achieve the meritorious effect of the present invention.

(Dextrin Fatty Acid Ester)

There is no limitation to the dextrin fatty acid ester employed in the present invention, such that it may be selected from esters constituted by dextrin and fatty acid or derivatives thereof. Examples of the dextrin fatty acid ester preferably include an ester having at least a partial structure in which a molecule of a C8 to C24 fatty acid is esterified to one of hydroxyl groups of a dextrin molecule, or the derivatives thereof, for example, an ester in which one or more C8 to C24 fatty acids is esterified to one or more hydroxyl groups of a dextrin molecule. The hydroxyl group of the ester thus obtained may or may not further be esterified by another fatty acid.

The esterification degree of the ester preferably is about 30 to 95% and more preferably is about 50 to 90%. If the esterification degree is less than 30%, oleophilicity is undesirably insufficient, whereas, if the esterification degree is higher than 95%, adhesion to the surface of the particulate powders is undesirably lowered, and therefore both cases are not preferable. Specifically, the esters may be enumerated by dextrin myristate, dextrin palmitate, dextrin stearate, dextrin coconut oil fatty acid ester, dextrin behenate, dextrin palmitate-2-ethylhexanoate and the like. Although the treating agent can be prepared by conventional methods, they may be readily acquired as commercial articles, such as "Rheopearl KL", "Rheopearl MKL", "Rheopearl TT", "Rheopearl KE" and "Rheopearl TL", manufactured by CHIBA FLOUR MILLING CO. LTD.

If the above-described various surface treating agents are used for constituting layer A (layer coated with the surface treating agent of the present invention), one or more of the compounds in the agents may be mixed for use as a surface treating agent to perform the targeted surface treating to constitute the coating layer (layer A).

(Organo Polysiloxane Modified at Sole Terminal End with Functional Group)

The organo polysiloxane modified at a sole terminal end with a functional group, such as the organo polysiloxane modified at a sole terminal end with a trialkoxy group, is preferably a compound having the following general formula (7):

$$(R^3{}_3SiO)(R^3{}_2SiO)_n(SiR^4{}_3) \qquad (7)$$

where plural $R^3$s in the above general formula are all independent of each other and respectively denote C1 to C10 saturated or unsaturated hydrocarbon residual groups, whereas plural $R^4$s in the above general formula are all independent of each other and respectively denote any one of a hydrogen atom, a hydroxyl group, a halogen atom (Cl, Br, I, etc.), silazane group, isopropenoxy group and 1 to 4 carbon atom lower alkoxy groups, n being an integer of 10 to 100.

If the value of n is less than 10, the reaction proceeds too quickly so that hydrolysis is accelerated, by the acidic point or basic point (isoelectric point) of the powder and/or trace quantities of moisture affixed to the powder surface, to cause cross-linking polymerization which causes the coating layer to become gelated or a semi-solid state and hence the targeted oily coating layer cannot be obtained. If the n value exceeds 100, reactivity is drastically lowered and the coating layer on the surface of the particulate powders becomes non-uniform. Therefore, dispersibility in the oleophilic liquid cannot be expected so that no contribution can be expected towards the hydrophobic property and oleophilicity.

As the surface treating agent for layer B, the products "X-24-9826", "X-24-9171" and "X-24-9174" manufactured by SHIN-ETSU CHEMICAL CO. LTD. may be conveniently purchased and used.

(Alkylsilane Modified at the Sole Terminal End with a Functional Group)

Among the alkylsilanes modified at the sole terminal end with a functional group, there are a variety of silane derivatives, such as alkyl trialkoxysilane modified at the sole terminal end with a functional group. The compound represented by the following general formula (8) is preferably employed:

$$R^5SiR^6{}_3 \qquad (8)$$

where $R^5$ preferably denotes an alkyl group having a 6 to 30 carbon atom straight chain or side chain, plural $R^6$s are independent of one another and respectively denote any one of a hydrogen atom, a hydroxyl group, a halogen atom, such as Cl, Br, I, etc. and a 1 to 4 number of carbon atom lower alkoxy group.

If the number of carbon atoms of $R^5$ is less than 6, no lubricious feeling can be obtained, whereas, if it exceeds 30, reactivity is drastically lowered such that the coating layer on the surface of the particulate powders tends to be non-uniform. The result is that dispersibility to the oleophilic liquid cannot be achieved so that no contribution is made to the hydrophobic nature and oleophilicity of the powders being treated. Moreover, the coating layer becomes a solid coating layer so that the meritorious effect of the present invention, that is the lubricious feeling, cannot be obtained.

The treating agent may conveniently be acquired as a marketed product, such as "TSL 8185" and "TSL8186" manufactured by TOSHIBA SILICONE CO. LTD., "SIO6645.0" manufactured by CHISSO CORPORATION, "KBM-3103" manufactured by SHIN-ETSU CHEMICAL CO. LTD. and "A-137" manufactured by NIPPON UNICAR CO. LTD.

(Branched Fatty Acid)

There is no limitation to the branched fatty acids employed in the present invention if the fatty acid used has a branched alkyl group. It is preferred to use 8 to 22 carbon atom branched fatty acids which are superior in dispersibility and which give an oily feeling when used on the powders. Examples of marketed products include isononanoic acid, 2-ethylhexoic acid, isotridecanoic acid, isomyristic acid, isopalmitic acid, isostearic acid and isobehenic acid. The branched fatty acids with the number of carbon atoms less than 8 or more than 22 are not desirable since the meritorious effect of the present invention is not achieved.

For the various surface treating agents described above, any one may be used, for the surface treating agents, or plural compounds for the surface treating agents may be used in combination.

The treating agent used for layer B is a compound which covers the outermost layer of the powdered material, so that it significantly affects the dispersibility or aesthetic feeling of the treated powders. This treating agent has a functional group only at the sole terminal end, such that an organopolysiloxane chain, straight alkyl chain or a branched alkyl chain, as a main chain molecule, becomes freely mobile.

The dispersibility into the oleophilic liquid and the lubricious feeling is due to a large extent to the length of this main chain. The organopolysiloxane modified at the sole terminal end with a functional group has a polymerization degree of the order of 10 to 100, whereas, with the alkylsilane modified at the sole terminal end with a functional group, the number of carbon atoms of the alkyl group is 6 to 30 and, with the branched fatty acid, the number of carbon atoms is of the order of 8 to 22, so that coating as applied gives surface-treated powders having a lubricious feeling and excellent (super)-dispersibility.

If the organo polysiloxane modified at the sole terminal end with a functional group, with the polymerization degree less than 10, is applied, the lubricious feeling and dispersibility is slightly lowered. Especially, in the case of dispersions into oleophilic liquids, the dispersibility and dispersion stability, which is the main characteristics of the present invention, cannot be achieved. It is hypothesized that the short length of the organo siloxane chain, directly affects and minimizes its affinity for oleophilic liquids.

If the range of the polymerization degree is too high, specifically exceeds 100, or the number of carbon groups of the alkyl group in the alkylsilane modified at the sole terminal end with a functional group or the branched fatty acid is excessive, (specifically the number of carbon atoms exceeds 30, and the number of carbon atoms exceeds 24, respectively), reactivity is drastically lowered, with the result that the degree of hydrophobic nature or oleophilicity is lowered to give a sticky, heavy feeling.

(On the Coating Amount for Powder)

Such an amount of the surface treating agent constituting a solid coating layer (layer A) on the surface of the particulate powder, which is just short of the amount to uniformly coat the particle surface is desirable. If the surface treating agent is of such a quantity as to uniformly cover the particle surface completely, the particle tends to become flocculated to neighbouring particles, which is not desirable. The amount of the surface treating agent just short of the amount which uniformly coats the particle surface, is such a coating amount which forms an emulsifying layer in a test on the coating uniformity, which is one of the evaluation items shown in the Examples in the specification of this application. This test is evaluated when layer A only, is applied to the powder.

In the present invention, layer A needs to be solid at room temperature because it is easier to coat the outermost surface of the particulate powder with the least amount of surface-treating agent to give an oleophilic uniform coating than with a liquid compound at room temperature. On the other hand, it is necessary for layer B to be liquid at room temperature because the outermost layer of the particulate powder must be liquid-like by coating the outermost layer of the particulate powder with a liquid molecule. It is also desirable that the particulate powders, while appearing to be powders, present a microscopic appearance that the particulate powders are dispersed in a liquid. The required coating quantity is selected to meet this condition.

It is hypothesized that even when these powder particles come close to each other, they do not become flocculated together because the particle surface is coated with these liquid molecules, to give excellent dispersibility. The surface of the particulate powder is already wet and hence is superior in affinity to the oleophilic liquid to present optimum dispersibility. In particular, it may be premeditated that, in an oleophilic liquid, layer B liquid molecules are stretched to their maximum length and dispersed throughout to obstruct contact between particles (steric hindrance) to achieve dispersion stability. The compounds for layers A and B are selected, depending on the system into which the powders to be coated are mixed into and on the type of the oleophilic liquid as the dispersion medium. For example, if it is desired to prepare a pressed powder without any addition of binders, layers A and B are coated with a dextrin fatty acid ester and with a branched fatty acid, respectively. If dispersibility in silicone oil is required, layers A and B are coated with an organo polysiloxane and with an organo polysiloxane modified at the sole terminal end with a functional group, respectively. If dispersibility in a volatile hydrocarbon is required, layers A and B are coated with a fatty acid and with an alkylsilane modified at the sole terminal end with a functional group. If dispersibility in an ester oil is required, layers A and B are coated with N-acylamino acid and with branched fatty acid, respectively.

In the present invention, the "oleophilic liquid" is an oily material, which is used as a cosmetic, which is liquid or solid at room temperature and which is difficult to solubilize in water. Specific examples of the oleophilic liquid are oils and fats, such as safflower oil, soybean oil, evening primrose oil, grapeseed oil, rose hip oil, ququinut oil, almond oil, sesame oil, wheat bran oil, corn oil, cottonseed oil, avogado oil, olive oil, camellia oil, pasic oil, castor oil, peanut oil, cobnut (hazelnut) oil, macademia nut oil, medoform oil, cacao fat, sear fat, wood wax, coconut oil, palm oil, palm kernel oil, beef fat, horse meat fat, mink oil, milk fat, egg yolk oil and turtle oil, waxes, such as bees wax, whale wax, lanolin, carnauba wax, candelilla wax and hohoba oil, hydrocarbons, such as fluid paraffin, fluid isoparaffin, squalane, squalene, vaseline, paraffin sericine and microcrystalline wax, fatty acids, such as lauric acid, myristic acid, palmitic acid, stearic acid, behenic acid, oleic acid, linolic acid, undecylenic acid, hydroxy stearic acid and lanolin fatty acid, higher alcohols, such as myristyl alcohol, cetyl alcohol, cetostearyl alcohol, stearyl alcohol, aralkyl alcohol, behenyl alcohol, oleyl alcohol, hohoba alcohol, batyl alcohol, cholesterol, phytosterol, lanolin alcohol and isostearyl alcohol, esters, such as ethyl oleate, isopropyl myristate, cetyl octanoate, diisostearyl malate and glyceryl tricaprylate, silicones, such as methyl polysiloxane, methyl phenyl polysiloxane and decamethyl cyclotetrasiloxane, organic solvents, such as ethyl acetate, butyl acetate and toluene, anionic, cationic, nonionic and amphoteric surface active agents (surfactants)

A preferred method for dispersing the coated powders of the present invention in an oleophilic liquid, that is a solid at room temperature may be to disperse the powders in the oleophilic liquid liquefied by heating to a temperature higher than its melting point (temperature). This method is commonly used for a capsule or a preparation form in which a larger amount of wax solid or the like at room temperature is mixed, such as in lipsticks.

The amount of the surface treating agent for forming the solid coating layer is preferably the same as that of the liquid surface treating agent on comparison based on weight or is less than that of the liquid surface treating agent ($A \leqq B$) Therefore, in coating the powder surface with the surface treating agent which gives a solid coating layer at room temperature, and in coating the powder surface with the surface treating agent which gives a liquid coating layer at room temperature, the mixing ratio of the respective coating layers for the powder is preferably set so that the amount in weight of the surface treating agent for the liquid coating layer (layer B) is equal to or greater than that of the surface treating agent for the solid coating layer (layer A).

If the amount in weight of the surface treating agent for the solid coating layer is larger than that of the surface treating agent for the liquid coating layer, the dispersibility of the resulting surface-treated powder in an oleophilic liquid may tend to be poor to some extent.

The amount of the surface treating agent for the solid coating layer is preferably a necessary minimum amount capable of uniformly coating the particulate powder, as described above. If this amount of the surface treating agent is larger than the necessary minimum amount, the particulate powder particles are simply flocculated, such that, if the particulate powder particles are coated with the surface treating agent for the coating layer that is a liquid at room temperature, it is not possible to achieve superior dispersibility in the oleophilic liquid of the produced surface-treated powder. Since the necessary minimum amount is varied with the powder type and with the treating method, it is necessary to check an appropriate coating amount by experimentation beforehand.

The coating amount of layer A that is a solid at room temperature differs with the type and the specific surface area of the powder treated according to the present invention. It is, however, preferably about 0.1 to 15 weight parts, more preferably about 0.1 to 10 weight parts and further more preferably about 0.5 to 6 weight parts in reference to 100 weights parts of the powder material prior to the surface treating (without the layers). If this amount of the surface treating agent is less than 0.1 weight part, it may not be possible to produce a uniform coating layer on the powder surface. On the other hand, if the coating amount exceeds 15 weight parts, the particulate powder particles may be simply flocculated, such that, even if the particulate powder particles might be coated with the surface treating agent for the coating layer liquid at room temperature, it may not be possible to achieve superior dispersibility in the oleophilic liquid of the produced surface-treated powder.

In a similar manner, the coating amount of the surface treating agent for layer B is preferably about 0.1 to 30 weight parts, more preferably about 0.5 to 20 weight parts and further more preferably about 0.5 to 15 weight parts, in reference to 100 weight parts of the powder material prior to the surface treating (without the layers). If the coating amount is lower than the above range, aesthetic feeling, adhesion to the skin and dispersibility are undesirably lowered. If the coating amount exceeds the above range, the amount of the free treating agent not reacted with the surface of the particulate powder particles is undesirably increased, however, the resulting surface-treated powder is not improved in dispersibility in the oleophilic liquid. Accordingly, such both cases are not preferable.

(Coating Method)

As a method for coating the powder with layer A, as a first layer, preferably a surface treating agent for forming a coating layer, preferably solid at room temperature, and further with layer B, as a second layer, preferably a surface treating agent for forming a coating layer, preferably liquid at room temperature, any suitable known methods in coating a surface treating agent may be used. The following are typical examples, of the coating method:

1. A dry method consisting of mixing e.g., a solid surface treating agent by a Henschel mixer, a super-mixer or the like, mixing a liquid surface treating agent to the resulting system and drying the resulting mixture;
2. A method consisting of dispersing the powder to be treated in water or in an organic solvent by a mechano-chemical type of mill, such as a ball mill, a sand grinder or the like, mixing and fixing e.g., a solid surface treating agent, further mixing e.g., a liquid surface treating agent into the system, removing the solvent and drying the resulting system (mixture); and
3. A method consisting in contacting the powder to be treated in a high-speed gas stream such as one obtained in a jet mill, with e.g., a solid surface treating agent for coating, and further contacting the resulting system with e.g., a liquid surface treating agent for coating, as described in Japanese Patent Kokoku Publication JP-B-6-59397 proposed by the present inventors, the whole content of which is incorporated in this specification by reference. In particular, a treating method by the jet method is preferably applied to the fine particulate powder having a primary particle size below a submicron diameter or equal to a submicron diameter.

It is sufficient if the "treating method" used herein in general may be a hydrophobic treating method applied to surface treating of the powdered material (substrate). Although the dispersibility in the oleophilic liquid is slightly inferior, it is possible to mix the surface treating agent (for layer A), preferably a solid at room temperature with the surface treating agent (for layer B), preferably a liquid at room temperature together and to make the resulting mixture to effect the coating simultaneously.

The powdered material (powder) to be surface-treated in accordance with the present invention may be coated with an oxide or a hydrous oxide of, for example, at least one of aluminium, calcium, magnesium, cerium, silicon, zirconium, titanium, zinc, iron, cobalt, manganese, nickel and tin, for improving compatibility with the surface treating agent and bonding tendency thereof thereto. In such case, the powder so coated corresponds to the powdered material to be coated or treated according to the present invention, that is the powdered material (substrate; base material) prior to coating with layer A in the present invention.

The amount of mixing of the so-produced coated powder to cosmetic is arbitrarily selected depending on the properties of the cosmetic. However, the mixing amount of the powder in the entire composition is preferably about 0.1 to 100 wt %, more preferably about 1 to 100 wt % and further more preferably about 1 to 99 wt %. It is possible for the oleophilic liquid to be contained in the total composition. For example, a trace amount of the fine particles of the zinc oxide, as an astringent, may be occasionally contained in an amount e.g., of 0.1 wt % or so in a cosmetic. On the other hand, loose powders and pressed powders or the like, usually mixed with an oily agent(s) in an amount of a few wt % in the entire formula, may be possibly formulated without mixing the corresponding oily agent(s) in the present invention.

Also, one or more of the coated powders obtained in accordance with the present invention may be mixed as appropriate to these coated powders.

In addition, it is more preferred to mix the coated powder of the present invention in e.g., cosmetic, without employing the powder used in other conventionally used powders, in order to demonstrate the meritorious effect of the present invention more prominently. However, routinely used powders may also be used as a mixture in a range not detracting from the meritorious effect of the present invention.

The cosmetic containing a powder having two coating layers, according to the present invention, may be enumerated by finishing cosmetic, such as in a powder foundation, liquid foundation, oily foundation, stick foundation, pressed powders, face powders, lipstick, lip gloss, cheek rouge, eye shadow, eye brow, eye liner, mascara, aqueous nail enamel, oily nail enamel, emulsion type nail enamel, enamel top coat, enamel base coat and the like, cosmetic for skin, such as emollient cream, cold cream, whitening cream, emulsion, aqueous cosmetic, cosmetic liquid, carmine emulsion (lotion), liquid face washing agent, face washing foam, face washing cream, face-washing powder, makeup cleansing, body gloss and the like, cosmetic for hair, such as hair gloss, hair cream, hair shampoo, hair rinse, hair color, hair brushing agents and the like, and others, for example, sunscreen cream, san-tan cream, emulsion, soap, bath agent, perfume and the like.

For the cosmetic to which the powders coated with two layers (layers A and B) of the surface treating agents are mixed in accordance with the present invention, pigment dispersing agents, oily agents, surfactants, UV absorbers, anti-septics, anti-oxidants, film forming agents, humidifying (moisture-retaining) agents, thickening agents, dyestuffs, pigments, perfumes and the like may be used if so desired.

This application is claiming the priority based on the Japanese patent applications serial Nos. 194570/1999 and 073261/2000, filed on Jul. 8, 1999and filed on Mar. 16, 2000, respectively and the contents of these 2 Japanese applications are incorporated in the specification of this application by reference, if necessary.

EXAMPLES

The present invention will be explained in detail with reference to Examples and Comparative Examples. The coated powders (surface-treated powders) of the present invention are referred to below as "MiBrid treated powders". They, of course, are not intended to limit the scope of the present invention.

Example 1

An illustrative method for producing the MiBrid treated powders in the present invention is shown herein below.

Example 1-1

MiBrid Treated Mica

To 100 weight parts of "mica M-102" manufactured by MERCK Japan were added 3 parts of a 50 wt % solution of trimethyl siloxy silicic acid, manufactured by SHIN-ETSU CHEMICAL CO. LTD. under the trade name of "KF-9002", and 10 weight parts of a 50 wt % aqueous solution of isopropanol. The resulting mass was mixed under vacuum at 80° C. for 30 minutes, using a jacketed high-speed Henschel. To the resulting mixture were added 3 weight parts of straight-chained dimethyl polysiloxane, with a polymerization degree of 20, having a trimethoxy group at its sole terminal end, manufactured by SHIN-ETSU CHEMICAL CO. LTD. under the trade name of "X-24-9174" and 5 weight parts of a 50 wt % aqueous solution of isopropanol. The resulting mass was mixed in vacuum at 100° C. for 60 minutes, using a jacketed high-speed Henschel, to produce a MiBrid treated mica.

Example 1-2

MiBrid Treated Sericite

The treating similar to that of Example 1-1 was carried out using sericite manufactured by SANSHIN MINING INDUSTRY CO. LTD. under the trade name of "FSE" in place of "mica M-102" in Example 1-1 to produce a MiBrid treated sericite.

Example 1-3

MiBrid Treated Talc

The treating similar to that of Example 1-1 was carried out using talc manufactured by ASADA MILLING CO. LTD. under the trade name of "JA-46R" in place of the mica in Example 1-1 to produce a MiBrid treated talc.

Example 1-4

MiBrid Treated Mica (Simultaneous Coating)

To 100 weight parts of "mica M-102" manufactured by MERCK JAPAN were added 3 weight parts of a 50 wt % solution of trimethyl siloxysilicic acid, manufactured by SHIN-ETSU CHEMICAL CO. LTD. under the trade name of "KF-9002" and 1.5 weight parts of straight-chained dimethyl polysiloxane, with a polymerization degree of 10 and having a trimethoxy group at its sole terminal end, manufactured by SHIN-ETSU CHEMICAL CO. LTD. under the trade name of "X-24-9174". To the resulting mixture were further added 15 weight parts of a 50% aqueous solution of isopropanol and the resulting mass was mixed together in vacuum at 100° C. for 60 minutes using a jacketed high-speed Henschel to produce a MiBrid treated mica.

Example 1-5

MiBrid Treated Mica Titanium

MiBrid treated mica titanium was produced in the same way as in Example 1-1 except using mica titanium, manufactured by MEARL Corporation under the trade name of "Cloisonné Orange" in place of mica in Example 1-1.

Example 1-6

MiBrid Treated Silica Beads

MiBrid treated silica beads were produced in the same way as in Example 1-1 except using silica beads, manufactured by CATALYSTS & CHEMICALS INDUSTRY CO. LTD. under the trade name of "P-1500" in place of mica.

Comparative Example 1

Typical manufacturing methods for producing powders coated only with a solid surface treating agent or with a liquid surface treating agent are shown below for comparison.

Comparative Example 1-1

Mica Obtained on Treating with Trimethyl Siloxy Silicic Acid: Solid

To 100 weight parts of "mica M-102" manufactured by MERCK JAPAN were added 6 weight parts of a 50 wt % solution of trimethyl siloxy silicic acid, manufactured by SHIN-ETSU CHEMICAL CO. LTD. under the trade name of "KF-9002" and 15 weight parts of a 50% aqueous solution of isopropanol and the resulting mass was mixed under vacuum at 100° C. for 60 minutes, using a jacketed high-speed Henschel to give a trimethyl siloxysilicic acid treated mica.

Comparative Example 1-2

Mica Obtained on Treating with Dimethyl Polysiloxane: Liquid

To 100 weight parts of "mica M-102", manufactured by MERCK JAPAN, were added 3 weight parts of straight-chained dimethyl polysiloxane, with a polymerization degree of 20, having a trimethoxy group at its sole terminal end, manufactured by SHIN-ETSU CHEMICAL CO. LTD. under the trade name of "X-24-9174" and 15 weight parts of a 50% aqueous solution of isopropanol, and the resulting mass was mixed in vacuum at 100° C. for 60 minutes to give a mica treated with dimethyl polysiloxane.

Comparative Example 1-3

Mica Titanium Obtained on Treating with Dimethyl Polysiloxane: Liquid

Mica titanium treated with dimethyl polysiloxane was produced in the same way as in Comparative Example 1-2 except using mica titanium, manufactured by MEARL Corporation under the trade name of "Cloisonné Orange" in place of the mica in Comparative Example 1-2.

Comparative Example 1-4

Sericite Treated with Trimethylsiloxy Silicic Acid: Solid

Sericite treated with trimethylsiloxy silicic acid was produced in the same way as in Comparative Example 1-1 except using sericite in place of the mica in Comparative Example 1-1.

Comparative Example 1-5

Talc Treated with Trimethylsiloxy Silicic Acid: Solid

Talc treated with trimethylsiloxy silicic acid was produced in the same way as in Comparative Example 1-1 except using talc in place of the mica in Comparative Example 1-1.

Comparative Example 1-6

Silica Beads Treated with Trimethylsiloxy Silicic Acid: Solid

Silica beads treated with trimethylsiloxy silicic acid was produced in the same way as in Comparative Example 1-1 except using silica beads in place of mica in Comparative Example 1-1.

Comparative Example 1-7

Mica Treated with Stearic Acid and with N-lauroyl-L-lysine: Solid

To 100 weight parts of "mica M-102", manufactured by MERCK JAPAN, were added 1.5 weight parts of stearic acid, manufactured by NOF CORPORATION KAISHA, LTD. under the trade name of "SK-1", and the resulting mass was mixed together at 80° C. for 15 minutes using a high-speed heater Henschel. To the resulting mixture were added 4 weight parts of N-lauroyl-L-lysine ("amihope LL"; manufactured by AJINOMOTO CO., INC.) and the resulting mixture was mixed together at 80° C. for 15 minutes. The resulting mass was heated to 105° C. and mixed together for three minutes to give a mica treated with stearic acid and N-lauroyl-L-lysine.

Example 2

A typical manufacturing method for MiBrid treated powders according to the present invention is explained for different types of powders.

Example 2-1

MiBrid Treated Titanium Dioxide

To 100 weight parts of titanium dioxide, manufactured by ISHIHARA SANGYO KAISHA CO. LTD. under the trade name of "CR-50" were added 2 weight parts of myristic acid manufactured by KAO CO. LTD. under the trade name of "LUNAC MY-98" and 20 weight parts of "IP-SOLVENT" manufactured by IDEMITSU PETROCHEMICAL CO. LTD. and the resulting mass was kneaded together under vacuum at 50° C. for 60 minutes using a vacuum kneader. To the resulting mixture were further added 3 weight parts of straight-chained dimethyl polysiloxane, with a polymerization degree of 50, having a trimethoxy group at its sole terminal end, manufactured by SHIN-ETSU CHEMICAL CO. LTD. under the trade name of "X-24-9826" and 30 weight parts of isopropyl alcohol under vacuum at 100° C. for 60 minutes. The resulting mixture was passed through an atomizer to give a MiBrid treated titanium dioxide.

Example 2-2

MiBrid Treated Yellow Iron Oxide

MiBrid treated yellow iron oxide was produced in the same way as in Example 2-1 except using yellow iron oxide manufactured by TITAN KOGYO KABUSHIKI KAISHA under the trade name of "MAPICO YELLOW LEMON" in place of the titanium dioxide and also using dextrin myristate manufactured by CHIBA FLOUR MILLING CO. LTD. under the trade name, "RHEOPEARL MK L" in place of myristic acid as a solid surface treating agent in Example 2-1.

Example 2-3

MiBrid Treated Red Iron Oxide

MiBrid treated red iron oxide was produced in the same way as in Example 2-1 except using red iron oxide manufactured by MORISHITA BENGARA CO. LTD. under the trade name of "BENGARA SHIPPO" in place of the titanium dioxide and also using isostearic acid, manufactured by HENKEL JAPAN CO. LTD. under the trade name of "isostearic acid 871" in place of a terminal trimethoxy dimethyl polysiloxane in Example 2-1 as a liquid surface treating agent.

Example 2-4

MiBrid Treated Black Iron Oxide

MiBrid treated black iron oxide was produced in the same way as in Example 2-1 except using black iron oxide manufactured by TITAN KOGYO KABUSHIKI KAISHA under the trade name of "BL-100" in place of the titanium dioxide in Example 2-1.

Comparative Example 2

Typical manufacturing methods for producing powders coated only with an abundant solid surface treating agent or only with an abundant liquid surface treating agent and the like are shown below for the sake of comparison.

Comparative Example 2-1

Coating with a Large Quantity of Solid Surface Treating Agent) Myristic Acid Treated Titanium Dioxide To 100 weight parts of titanium dioxide, manufactured by ISHIHARA SANGYO KAISHA CO. LTD. under the trade name of "CR-50", 6 weight parts of myristic acid manufactured by KAO CO. LTD. under the trade name of "LUNAC MY-98" and 20 weight parts of methylethylketone were added and the resulting mass was kneaded under vacuum at 100° C. for 60 minutes using a vacuum kneader. The resulting kneaded mass was passed through an atomizer to yield myristic acid treated titanium dioxide.

Comparative Example 2-2

Coating with a Large Quantity of Solid Surface Treating Agent) Dimethyl Polysiloxane Treated Titanium Dioxide To 100 weight parts of titanium dioxide, manufactured BY ISHIHARA SANGYO KAISHA CO. LTD. under the trade name of "CR-50", 6 weight parts of straight-chained dimethyl polysiloxane with a polymerization degree of 50 and having a trimethoxy group at a sole terminal end, manufactured by SHIN-ETSU CHEMICAL CO. LTD. under the trade name of "X-24-9826" and 30 weight parts of isopropyl alcohol, were added and the resulting mass was kneaded under vacuum at 100° C. for 60 minutes using a vacuum kneader. The resulting kneaded mass was passed through an atomizer to yield dimethyl polysiloxane treated titanium dioxide.

Comparative Example 2-3

Coating of a Liquid Oily Agent as the Second Layer) Titanium Dioxide Treated with Myristic Acid and Dimethyl Polysiloxane In Example 2-1, the titanium dioxide was coated with a solid surface treating agent of myristic acid and added to with 3 weight parts of non-reactive straight-chained dimethyl polysiloxane, with a polymerization degree of approximately 50, manufactured by SHIN-ETSU CHEMICAL CO. LTD. under the trade name of "KF-96" (100 cs) and with 30 weight parts of isopropyl alcohol. The resulting mass was kneaded together in vacuum at 100° C. for 60 minutes and passed through an atomizer to yield titanium dioxide treated with both myristic acid and dimethyl polysiloxane.

Comparative Example 2-4

Yellow Iron Oxide Treated with Myristic Aid and Dimethyl Polysiloxane

Yellow iron oxide treated with myristic acid and dimethyl polysiloxane was produced in the same way as in Comparative Example 2-2 except using yellow iron oxide in place of the titanium dioxide in Comparative Example 2-2.

Comparative Example 2-5

Red Iron Oxide Treated with Myristic Acid and Dimethyl Polysiloxane

Red iron oxide treated with myristic acid and dimethyl polysiloxane was produced in the same way as in Comparative Example 2-2 except using red iron oxide manufactured by MORISHITA BENGARA CO. LTD. under the trade name of "BENGARA SHIPPO" in place of titanium dioxide in Comparative Example 2-2.

Example 3

In the following, several examples of the manufacturing method for the MiBrid treated powders according to the present invention are given in connection with fine particulate powders having a primary particle size not more than a submicron.

Example 3-1

MiBrid Treated Fine Particulate Titanium Dioxide

To 100 weight parts of fine particulate titanium dioxide, manufactured by ISHIHARA SANGYO KAISHA CO. LTD. under the trade name of "TTO-55A" was added a dissolved mass of 2 weight parts of lecithin manufactured by ASAHI CHEMICAL INDUSTRY CO. LTD. under the trade name of "LECITHIN 5" in 3 weight parts of hot water at 80° C. and mixed together for five minutes using a Henschel mixer. The resulting mixture was pulverized and treated concurrently using a jet mill (100 AFG type manufactured by ALPINE AG. of Germany) and further admixed with 4 weight parts of octadecyl trimethoxy silane, the alkyl group of which has 18 carbon atoms, manufactured by TOSHIBA SILICONE CO. LTD. under the trade name of "TSL 8186". The resulting mass was mixed by a Henschel mixer for five minutes. The resulting mixture was further pulverized and treated concurrently by a jet mill and dried at 130° C. for seven hours to yield MiBrid treated fine particulate titanium dioxide.

Example 3-2

MiBrid Treated Fine Particulate Zinc Oxide 100 weight parts of fine particulate zinc oxide, manufactured by SAKAI CHEMICAL INDUSTRY CO. LTD. under the trade name of "FINEX-50" and 3 weight parts of polyethylene maleate, manufactured by NIPPON PETROCHEMICALS CO. LTD. under the trade name of "POWAX S-30", were mixed together for five minutes by a heater Henschel after the temperature of the system (the composition) reached 60° C. The resulting mixture was pulverized and treated concurrently using a jet mill (100 AFG type manufactured by ALPINE AG. of Germany) To the resulting mixture were added 4 weight parts of octadecyl trimethoxy silane, the alkyl group of which has 18 carbon atoms, manufactured by TOSHIBA SILICONE CO. LTD. under the trade name of "TSL8186". The resulting mixture was mixed together for five minutes using a Henschel mixer. The resulting mixture was further pulverized and treated concurrently using a jet mill, and then dried at 130° C. for seven hours to yield a MiBrid treated fine particulate zinc oxide.

Example 3-3

MiBrid Treated Fine Particulate Titanium Dioxide (in Case the Quantity of the Solid Surface Treating Agent is Larger than that of the Liquid Surface Treating Agent)

In Example 3-1, the quantity of lecithin was increased to 4 weight parts in carrying out same treating as in Example 3-1. 2 weight parts of octadecyl trimethoxy silane were added further to the resulting mixture to carry out same treating as in Example 3-1 to yield a MiBrid treated fine particulate titanium dioxide.

Example 3-4

MiBrid Treated Fine Particulate Zinc Oxide 100 weight parts of fine particulate zinc oxide, manufactured by SAKAI CHEMICAL INDUSTRY CO. LTD. under the trade name of "FINEX-50", and 3 weight parts of polyethylene maleate, manufactured by NIPPON PETROCHEMICALS CO. LTD. under the trade name of "POWAX S-30", were mixed together for five minutes in a heater Henschel, after the temperature of the system (the composition) reached 60° C. The mixture was pulverized and treated concurrently in a jet mill, and admixed with 5 weight parts of octadecyl trimethoxy silane, of which the alkyl group has the number of carbon atoms being 18, and with 5 weight parts of straight-chained dimethyl polysiloxane, with the polymerization degree of 50, having a trimethoxy group at a sole terminal end. The resulting mixture was mixed together for five minutes by a Henschel mixer and subsequently pulverized and treated simultaneously using a jet mill so as to be then dried at 130° C. for seven hours to yield MiBrid treated fine particulate zinc oxide.

Example 3-5

MiBrid Treated Fine Particulate Zinc Oxide 100 weight parts of fine particulate zinc oxide, manufactured BY SAKAI CHEMICAL INDUSTRY CO. LTD. under the trade name of "FINEX-50" and 3 weight parts of polyethylene maleate manufactured by NIPPON PETROCHEMICALS CO. LTD. under the trade name of "POWAX S-30" were mixed together for five minutes by a heater Henschel after the temperature of the system reached 60° C. Further, 5 weight parts of octadecyl trimethoxy silane, of which the alkyl group has 18 carbon atoms, and 5 weight parts of straight-chained dimethyl polysiloxane, with the polymerization degree of 50, having a trimethoxy group at a sole terminal end, were added thereto. The resulting mixture was mixed together for 5 minutes by a Henschel mixer. The mixture was further pulverized and treated simultaneously using a jet mill, and dried at 130° C. for seven hours to yield MiBrid treated fine particulate zinc oxide.

Comparative Example 3

In the following, some examples for manufacture of a powder coated with a surface treating agent wherein the polymerization degree of the alkysilane described above is 8 are shown.

Comparative Example 3-1

Alkylsilane Treated Fine Particulate Titanium Dioxide

According to the process in Example 1 for the production described in the Japanese Patent Kokai Publication JP-A-8-92052, fine particulate titanium dioxide, manufactured by ISHIHARA SANGYO KAISHA CO. LTD. under the trade name of "TTO-55A" was surface-treated with 6 weight parts of octyltrimethoxy silane, of which the alkyl group has 8 carbon atoms, to yield alkyl silane treated fine particulate titanium dioxide.

Comparative Example 3-2

Alkylsilane Treated Fine Particulate Titanium Dioxide

Alkylsilane treated fine particulate titanium dioxide was obtained in the same way as in Example 3-1 except using butyltrimethoxy silane, of which the alkyl group has the number of carbons being 4, manufactured by CHISSO CORPORATION under the trade name of "SIB1988.0", in place of the octadecyl trimethoxy silane, of which the alkyl group has 18 carbon atoms in Example 3-1, to yield alkylsilane treated fine particulate titanium dioxide.

Comparative Example 3-3

Alkylsilane Treated Fine Particulate Zinc Oxide

Alkylsilane treated fine particulate zinc oxide was produced in the same way as in Example 3-2 except using the butyl trimethoxy silane in place of the octadecyl trimethoxy silane in Example 3-2.

The MiBrid treated powders in the present invention obtained as described above and the powders treated in accordance with the Comparative Examples were evaluated by the following testing method. The results are shown in Table 1 (A) to (C) and in Table 2.

TABLE 1

| (A) Sample No. | Coating Uniformity | Oily Agent A Wetting Point | Oily Agent A Fluid Point | Particle Size ($\mu$m) D 5 0 | Particle Size ($\mu$m) D 9 5 |
|---|---|---|---|---|---|
| Example 1-1 | ◯ | 35 | 45 | 7.357 | 17.269 |
| Example 1-2 | ◯ | 30 | 42 | 5.687 | 14.952 |
| Example 1-3 | ◯ | 38 | 45 | 8.826 | 26.340 |
| Example 1-4 | ◯ | 38 | 48 | 7.688 | 18.654 |
| Example 1-5 | ◯ | 30 | 40 | 10.565 | 35.870 |
| Example 1-6 | ◯ | 65 | 74 | 5.687 | 9.269 |
| Comp. Ex. 1-1 | △ | 42 | 60 | 9.562 | 25.489 |
| Comp. Ex. 1-2 | X | 40 | 54 | 9.023 | 22.219 |
| Comp. Ex. 1-3 | X | 35 | 47 | 12.345 | 38.658 |
| Comp. Ex. 1-4 | △ | 42 | 60 | 7.523 | 16.187 |
| Comp. Ex. 1-5 | △ | 50 | 71 | 9.236 | 30.158 |
| Comp. Ex. 1-6 | X | 70 | 103 | 7.225 | 15.361 |
| Comp. Ex. 1-7 | ◯ | 45 | 60 | 11.251 | 30.818 |
| Example 2-1 | ◯ | 18 | 25 | 0.632 | 5.623 |
| Example 2-2 | ◯ | 35 | 44 | 0.851 | 6.855 |
| Example 2-3 | ◯ | 32 | 47 | 0.621 | 5.123 |
| Example 2-4 | ◯ | 30 | 40 | 0.741 | 7.698 |
| Comp. Ex. 2-1 | X | 25 | 36 | 1.542 | 20.235 |
| Comp. Ex. 2-2 | △ | 20 | 27 | 1.213 | 15.221 |
| Comp. Ex. 2-3 | X | 28 | 41 | 2.056 | 20.003 |
| Comp. Ex. 2-4 | X | 38 | 50 | 1.254 | 7.698 |
| Comp. Ex. 2-5 | X | 30 | 40 | 0.963 | 6.887 |
| Example 3-1 | ◯ | 48 | 67 | 0.378 | 3.875 |
| Example 3-2 | ◯ | 52 | 70 | 0.305 | 3.548 |
| Example 3-3 | ◯ | 55 | 76 | 0.401 | 4.205 |
| Example 3-4 | ◯ | 40 | 55 | 0.350 | 3.792 |
| Example 3-5 | ◯ | 42 | 57 | 0.353 | 3.804 |
| Comp. Ex. 3-1 | ◯ | 60 | 91 | 1.845 | 6.319 |
| Comp. Ex. 3-2 | △ | 58 | 84 | 1.773 | 6.257 |
| Comp. Ex. 3-3 | X | 78 | 110 | 0.415 | 5.329 |

| (B) Sample No. | Oily Agent B Wetting Point | Oily Agent B Fluid Point | Particle Size ($\mu$m) D 5 0 | Particle Size ($\mu$m) D 9 5 |
|---|---|---|---|---|
| Example 1-1 | 37 | 49 | 7.564 | 17.810 |
| Example 1-2 | 32 | 45 | 5.712 | 15.663 |
| Example 1-3 | 40 | 45 | 8.899 | 26.778 |

TABLE 1-continued

| Sample No. | | | | |
|---|---|---|---|---|
| Example 1-4 | 38 | 48 | 7.823 | 18.874 |
| Example 1-5 | 35 | 43 | 11.356 | 36.271 |
| Example 1-6 | 68 | 78 | 5.865 | 9.810 |
| Comp. Ex. 1-1 | 45 | 68 | 10.469 | 25.877 |
| Comp. Ex. 1-2 | 41 | 57 | 9.598 | 23.258 |
| Comp. Ex. 1-3 | 40 | 50 | 13.002 | 38.669 |
| Comp. Ex. 1-4 | 40 | 58 | 7.335 | 16.025 |
| Comp. Ex. 1-5 | 50 | 70 | 9.165 | 30.987 |
| Comp. Ex. 1-6 | 75 | 107 | 7.711 | 15.663 |
| Comp. Ex. 1-7 | 40 | 61 | 11.368 | 30.145 |
| Example 2-1 | 22 | 30 | 0.688 | 5.712 |
| Example 2-2 | 35 | 43 | 0.865 | 6.933 |
| Example 2-3 | 32 | 45 | 0.573 | 5.662 |
| Example 2-4 | 30 | 40 | 0.782 | 7.865 |
| Comp. Ex. 2-1 | 27 | 40 | 1.668 | 21.631 |
| Comp. Ex. 2-2 | 19 | 30 | 1.350 | 15.430 |
| Comp. Ex. 2-3 | 30 | 45 | 2.132 | 22.305 |
| Comp. Ex. 2-4 | 41 | 53 | 1.206 | 7.321 |
| Comp. Ex. 2-5 | 33 | 42 | 0.956 | 6.237 |
| Example 3-1 | 45 | 62 | 0.353 | 3.425 |
| Example 3-2 | 50 | 65 | 0.202 | 2.858 |
| Example 3-3 | 55 | 73 | 0.374 | 3.903 |
| Example 3-4 | 43 | 57 | 0.362 | 3.886 |
| Example 3-5 | 45 | 61 | 0.369 | 3.909 |
| Comp. Ex. 3-1 | 58 | 90 | 1.542 | 5.889 |
| Comp. Ex. 3-2 | 55 | 80 | 1.336 | 6.001 |
| Comp. Ex. 3-3 | 70 | 103 | 0.390 | 4.995 |

| (C) Sample No. | Oily Agent C | | | |
|---|---|---|---|---|
| | Wetting Point | Fluid Point | Particle Size ($\mu$m) | |
| | | | D 5 0 | D 9 5 |
| Example 1-1 | 40 | 50 | 7.923 | 19.520 |
| Example 1-2 | 33 | 46 | 5.966 | 18.231 |
| Example 1-3 | 40 | 45 | 8.958 | 27.251 |
| Example 1-4 | 40 | 50 | 7.969 | 19.878 |
| Example 1-5 | 38 | 47 | 12.682 | 38.658 |
| Example 1-6 | 70 | 80 | 5.112 | 9.520 |
| Comp. Ex. 1-1 | 47 | 70 | 10.776 | 26.323 |
| Comp. Ex. 1-2 | 42 | 59 | 9.783 | 25.463 |
| Comp. Ex. 1-3 | 43 | 52 | 14.213 | 39.366 |
| Comp. Ex. 1-4 | 45 | 62 | 7.668 | 16.996 |
| Comp. Ex. 1-5 | 54 | 73 | 9.036 | 29.560 |
| Comp. Ex. 1-6 | 73 | 105 | 7.986 | 15.123 |
| Comp. Ex. 1-7 | 43 | 60 | 12.163 | 31.567 |
| Example 2-1 | 25 | 33 | 0.705 | 6.377 |
| Example 2-2 | 45 | 51 | 0.890 | 7.564 |
| Example 2-3 | 30 | 40 | 0.498 | 5.022 |
| Example 2-4 | 33 | 43 | 0.806 | 8.221 |
| Comp. Ex. 2-1 | 24 | 35 | 1.501 | 19.373 |
| Comp. Ex. 2-2 | 23 | 40 | 1.561 | 16.787 |
| Comp. Ex. 2-3 | 30 | 51 | 2.230 | 22.457 |
| Comp. Ex. 2-4 | 46 | 70 | 1.306 | 7.661 |
| Comp. Ex. 2-5 | 38 | 56 | 1.003 | 6.558 |
| Example 3-1 | 40 | 60 | 0.321 | 2.953 |
| Example 3-2 | 48 | 62 | 0.195 | 2.668 |
| Example 3-3 | 50 | 68 | 0.370 | 3.520 |
| Example 3-4 | 43 | 55 | 0.352 | 3.778 |
| Example 3-5 | 45 | 58 | 0.359 | 3.861 |
| Comp. Ex. 3-1 | 56 | 85 | 1.052 | 5.662 |
| Comp. Ex. 3-2 | 54 | 75 | 1.236 | 5.854 |
| Comp. Ex. 3-3 | 65 | 100 | 0.352 | 4.511 |

TABLE 2

| Sample No. | M I U | Whiteness Degree or L, a, b Value | in-vitro SPF Value | Optical Characteristics 0° + 45° | |
|---|---|---|---|---|---|
| Example 1-1 | 1.92 | — | — | 12.3 | 68.4 |
| Example 1-2 | 2.23 | — | — | 15.6 | 53.2 |
| Example 1-3 | 2.68 | — | — | 25.6 | 47.2 |
| Example 1-4 | 2.13 | — | — | 11.7 | 65.9 |
| Example 1-5 | 3.06 | — | — | — | — |
| Example 1-6 | 1.52 | — | — | 8.5 | 11.5 |
| Comp. Ex. 1-1 | 2.71 | — | — | 15.6 | 50.1 |
| Comp. Ex. 1-2 | 2.35 | — | — | 13.8 | 56.4 |
| Comp. Ex. 1-3 | 3.35 | — | — | — | — |
| Comp. Ex. 1-4 | 2.95 | — | — | 19.1 | 40.6 |
| Comp. Ex. 1-5 | 3.05 | — | — | 33.7 | 40.6 |
| Comp. Ex. 1-6 | 1.87 | — | — | 12.1 | 15.9 |
| Comp. Ex. 1-7 | 1.90 | — | — | 16.2 | 48.5 |
| Example 2-1 | 2.68 | 71 | — | — | |
| Example 2-2 | 2.57 | 72.1, 1.6, 43.2 | — | — | |
| Example 2-3 | 2.95 | 68.5, 42.1, 3.6 | — | — | |
| Example 2-4 | 3.05 | — | — | — | |
| Comp. Ex. 2-1 | 3.32 | 32 | — | — | |
| Comp. Ex. 2-2 | 2.91 | 56 | — | — | |
| Comp. Ex. 2-3 | 3.01 | 48 | — | — | |
| Comp. Ex. 2-4 | 2.87 | 75.6, 1.9, 36.5 | — | — | |
| Comp. Ex. 2-5 | 3.33 | 72.8, 36.9, 2.5 | — | — | |
| Example 3-1 | 3.52 | — | 38.7 | — | |
| Example 3-2 | 3.76 | — | 10.5 | — | |
| Example 3-3 | 3.85 | — | 9.7 | — | |
| Example 3-4 | 3.66 | — | 14.5 | | |
| Example 3-5 | 3.78 | — | 12.2 | | |
| Comp. Ex. 3-1 | 4.24 | — | 18.3 | — | |
| Comp. Ex. 3-2 | 4.55 | — | 5.7 | — | |
| Comp. Ex. 3-3 | 4.63 | — | 3.0 | — | |

(1) Test on Coating Uniformity 50 cc of water and 50 cc of hexane and further 0.5 g of a powder sample were charged in a transparent glass vial of 100 cc, which then was plugged. The vial was then shaken strongly by hand twenty times and allowed to stand at 50° C. for one week. The vial was then further stirred strongly by hand twenty times. After the vial was allowed to stand still for some time, the powder was observed and evaluated by the following three grades:

No transfer to the water phase has occurred: ○
An emulsion layer has been produced: Δ
Transfer to the water phase has occurred: X (2) Oil Absorption To each 20 g powder sample were applied dropwise, in small amounts, an oily agent A: dimethyl polysiloxane, 20 cs, manufactured by SHIN-ETSU CHEMICAL CO. LTD. under the trade name of "KF-96", an oily agent B: isotridecyl isononanoate, manufactured by NIHON EMULSION CO. LTD. under the trade name of "INTD-139", and an oily agent C: fluid paraffin manufactured by ESSO-STANDARD OIL INC. under the trade name of "CRISTOL 72", charged in a burette of 100 cc in capacity, and kneaded together with a spatula. The quantity of the oily agent (%) at which each powder sample was thoroughly wet with each oily agent was used as the wetting point. The quantity of the oily agent at which the powder sample commences to flow with the oily agent on applying the oily agent was used as the fluid (pour) point.

(3) Particle Size

For the sample in the fluid point, prepared by the oil absorption quantity test of (2) described above, D50 and D95 were measured using a high concentration particle size measurement device of a laser diffraction particle size measurement device manufactured by SHIMADZU under the trade name of "SALD-2000J".

(4) Aesthetic Feel (Using Touch; Lubricity)

On a 8 cm×5 cm collagen paper sheet, manufactured by IDEMITSU PETROCHEMICAL CO. LTD. under the trade name of "SUPPLALE", a powder material was coated at an amount of 1 mg/cm$^2$ and the resulting set was placed on a reciprocating dynamic frictional coefficient measurement tester manufactured by KATOTEC CO. LTD. The non-coated collagen paper sheet was placed thereon and a load of 50 g/cm$^2$ was applied to the entire system to measure an average value of the dynamic frictional coefficient (MIU) after carrying out five reciprocal motions.

(5) Covering Power 10 g of pigment grade titanium dioxide, obtained with the above Example and the Comparative Example, 0.5 g of carbon black, manufactured by MITSUBISHI CHEMICAL CORPORATION and 79.5 g of "TALC JA-46R", manufactured by ASADA MILLING CO. LTD., were mixed together and pulverized by an atomizer. To the resulting product were mixed 10 g of dimethylpolysiloxane (100 cs) manufactured by SHIN-ETSU CHEMICAL CO. LTD. under the trade name of "KF-96", to give a mixture which then was pulverized by an atomizer. For each sample, the whiteness degree was measured by a color difference meter manufactured by NIPPON DENSHOKU INDUSTRIES CO. LTD. under the trade name of "SZ-Σ90".

(6) Coloring Power 3 g of red iron oxide and yellow iron oxide, obtained in the Example and in the Comparative Example, 10 g of titanium dioxide manufactured by ISHIHARA SANGYO KAISHA CO. LTD. under the trade name of "CR-50" and 77.0 g of "TALC JA-46R" manufactured by ASADA MILLING CO. LTD. were mixed together and pulverized by an atomizer. To the resulting system were added 10 g of dimethylpolysiloxane (100 cs) manufactured by SHIN-ETSU CHEMICAL CO. LTD. under the trade name of "KF-96" and the resulting system was pulverized by an atomizer. For each sample, L, a, and b values were measured by a color analyzer manufactured by NIPPON DENSHOKU INDUSTRIES CO. LTD. under the trade name of "SZ-Σ90".

(7) In-vitro SPF Value Measurement 1 g each of samples of the fine particulate titanium dioxide and fine particulate zinc oxide, obtained in the Example and the Comparative Example described above was taken and mixed with 9 g of polybutene manufactured by NOF CORPORATION KAISHA, LTD. The resulting mixture was mixed with a spatula and dispersed by Hoover Muller under a condition of 25 revolutions for each sample with a load of 22.68 kg. This paste was then used to measure SPF values using an SPF analyzer manufactured by OPTOMETORICS, USA, under the trade name of "SPF ANALYZER 290S".

(8) Optical Characteristics 10 g of isotridecyl isononanoate were added to 90 g of a coated powder and mixed for one minute in a mixer of household use. The resulting product was then pulverized by an atomizer for use as a measurement sample for measuring optical characteristics. The sample under measurement was coated on an 8 cm by 5 cm collagen paper sheet manufactured by IDEMITSU PETROCHEMICAL CO. LTD. under the trade name of "SUPPLALE" at an amount of 2 mg/cm$^2$. With this coated film, the reflectance ratio at 0° and 45° was measured with the incidence light at −45° using a variable angle gloss meter manufactured by NIPPON DENSHOKU INDUSTRIES CO. LTD. under the trade name of "VGS-300A".

As samples for this measurement, mica, sericite and silica beads produced in the Example and in the Comparative Example were used.

As may be seen from Tables 1 and 2, the coated powder of the present invention (surface-treated powder) are good in affinity and superior in dispersibility with respect to oleophilic liquids, such that the functions of the powder base (powdered material), for example, aesthetic feeling (using touch, sliding property), covering power, coloring power, UV ray shielding power and optical characteristics can be improved appreciably.

It is noted that the lower the wetting point and the fluid point in the evaluation of the quantity of oil absorption, the higher its affinity for the oily agent, that is the smaller the quantity of oil absorption the better is its affinity to the oily agent. Furthermore, the smaller the particle size of the sample at the fluid point in the measurement of the quantity of oil absorption for the same powder, the better is its dispersibility even with samples with the same quantity of oil absorption or with samples with different quantities of oil absorption. As for the aesthetic feeling (using touch), covering power, coloring power and the SPF value, among the items of evaluation, the larger the numerical values, the higher is its function of the powder material which is displayed. As for the optical characteristics (properties), tests were conducted on the powder of mica, sericite, and talc having lamellar particle shape and spherically shaped powder of silica beads. The lamellar powder could be evaluated as to the state of dispersion of the particulate powder particles by evaluating the mirror surface reflection, whilst the spherically-shaped powder could be evaluated as to the state of dispersion of the particulate powders by evaluating the matted look.

In the case of the lamellar powdered material, the higher the 45° reflectance ratio (mirror surface reflectance ratio) and the higher the 45°–0° reflectance ratio, the better the particulate powder is in its dispersed state.

In the case of the spherically shaped powder, the higher the 0° reflectance ratio, the more the particulate powder is flocculated, whereas the lower the 45°–0° reflectance ratio value, the particulate powder looks matte and therefore is considered well dispersed.

Example 4

Production of a 2-way Powder Foundation

A 2-WAY powder foundation, having the composition shown in Table 3, was produced by the following method.

TABLE 3

| ingredients | weight parts |
| --- | --- |
| (1) red iron oxide (Example 2-3) | 1.5 |
| (2) yellow iron oxide (Example 2-2) | 2.8 |
| (3) black iron oxide (Example 2-4) | 0.1 |
| (4) titanium dioxide (Example 2-1) | 8.0 |
| (5) sericite (Example 1-2) | 26.0 |
| (6) talc (Example 1-3) | balance |
| (7) mica (Example 1-1) | 6.0 |
| (8) octyldodecyl myristate | 5.7 |
| (9) squalane | 2.5 |
| (10) methyl phenyl polysiloxane | 5.3 |
| (11) antiseptics | moderate |
| (12) perfume | moderate |

(Formulating Procedure)

The above ingredients (1) to (7) were mixed together and passed through a pulverizer. The resulting system (mixture) was transferred to a high-speed blender to which were also charged ingredients (8) to (12) and mixed together under heating to form a homogeneous state. The resulting mixture was homogenized on mixing and passed through a pulverizer and sieve to adjust the particle size. The resulting product was compressed and molded to produce a 2-way foundation.

Example 5

Production of an Emulsion Type Foundation

An emulsion type foundation of the composition shown in Table 4 was produced by the following method.

TABLE 4

| ingredients | weight parts |
| --- | --- |
| (1) decamethyl cyclopentasiloxane | 22.0 |
| (2) vaseline | 2.0 |
| (3) methyl phenyl polysiloxane | 6.0 |
| (4) squalane | 5.0 |
| (5) isooctyl isononanoate | 6.0 |
| (6) dimethyl polysiloxane polyoxyalkylene polymer (HLB = 3.5) | 3.5 |
| (7) red iron oxide (Example 2-3) | 1.6 |
| (8) yellow iron oxide (Example 2-2) | 2.5 |
| (9) black iron oxide (Example 2-4) | 0.1 |
| (10) titanium dioxide (Example 2-1) | 8.5 |
| (11) talc (Example 1-3) | 2.5 |
| (12) ethanol | 5.0 |
| (13) 1,3 butylene glycol | 5.0 |
| (14) sodium chloride | 2.0 |
| (15) purified water | balance |
| (16) antiseptics | moderate |
| (17) perfume | moderate |

(Formulating Procedure)

The above ingredients (7) to (11) were previously mixed together and pulverized. The mixture of the previously pulverized ingredients (7) to (11) was added to an oily phase obtained on homogeneously dissolving and mixing ingredients (1) to (6) at 70° C. and homogeneously dispersed in a homo-disper. An aqueous phase obtained on homogeneously mixing and dissolving the ingredients (12) to (16) at 70° C. was gradually added to the oily phase, homogeneously dispersed in a homo-mixer, cooled and added to with the ingredient (17) to adjust the emulsified particles to produce a liquid foundation.

Example 6

Production of a Pressed Powder

A pressed powder of the composition shown in Table 5 was produced by the following method.

TABLE 5

| ingredients | weight parts |
| --- | --- |
| (1) mica (Example 1-1) | 25.0 |
| (2) talc (Example 1-3) | to 100.0 |
| (3) sericite (Example 1-2) | 10.0 |
| (4) titanium dioxide (Example 2-1) | 1.5 |
| (5) perfume | moderate |

(Formulating Procedure)

The above ingredients (1) to (5) were evenly mixed to give a base of powdered cosmetic. 55 wt % of ethanol were mixed in reference to the weight of the powdered cosmetic base and mixed homogeneously. The resulting mixture was charged into a pan and compressed and molded under suction to give a molded product which then was dried at 40° C. for 24 hours to produce a solid white powder.

Example 7

Production of Powdered Eye Shadow

A powdered eye shadow, having the composition shown in Table 6, was produced by the following method:

TABLE 6

| ingredients | weight parts |
| --- | --- |
| (1) sericite (Example 1-2) | 25.0 |
| (2) mica (Example 1-4) | 10.0 |
| (3) mica titanium (Example 1-5) | 6.5 |
| (4) colored pigment (Examples 2-2, 3 and 4) | moderate |
| (5) squalane | 8.7 |
| (6) dimethyl polysiloxane | 2.5 |
| (7) PEG/MOD* | 8.0 |
| (8) sericine wax | 3.5 |
| (9) sorbitan tristearate | 1.0 |
| (10) perfume | moderate |

*purified ester gum/octyl dodecyl myristate = 50/50 mixture (SHIN-EI KAGAKU Co. LTD.).

(Formulating Procedure)

Of the above ingredients, ingredients (1) to (4), other than mica titanium, were mixed by a Henschel mixer and pulverized with an atomizer. To the resulting powder, mica titanium of ingredient (3) was added and mixed, and the ingredients (5) to (10) homogenized together were added thereto and mixed uniformly. The resulting mixture was pulverized by an atomizer and passed through a sieve so as to be then compressed and molded in a pan to produce a powdered eye shadow.

Example 8

Production of a Cheek Rouge

A cheek rouge having the composition shown in table 7 was produced by the following method:

TABLE 7

| ingredients | weight parts |
| --- | --- |
| (1) red iron oxide (Example 2-3) | 0.4 |
| (2) yellow iron oxide (Example 2-2) | 3.0 |
| (3) black iron oxide (Example 2-4) | 0.1 |
| (4) red No. 202* | 2.0 |
| (5) titanium dioxide (Example 2-1) | 10.0 |
| (6) mica (Example 1-1) | 55.0 |
| (7) zinc stearate | 1.0 |
| (8) fluid paraffin | 5.0 |
| (9) methyl polysiloxane (6 cs) | 7.0 |
| (10) vaseline | 1.0 |
| (11) anti-septics | moderate |
| (12) perfume | moderate |

*non-treated product (Formulating Procedure)

The above ingredients (1) to (7) were mixed together and passed through a pulverizer. The resulting powder was transferred to a high-speed blender where ingredients (8) to (12), heated and mixed together homogeneously, were added and mixed further together to a homogeneous state. The resulting mixture was passed through a pulverizer and sieved to adjust the particle size. The resulting product was compressed and molded to produce a cheek rouge.

Example 9

Production of an Oily Foundation

An oily foundation, having the composition shown in Table 8, was produced by the following method:

TABLE 8

| ingredients | weight parts |
| --- | --- |
| (1) isopropyl palmitate | 20.0 |
| (2) cetanol | 7.0 |
| (3) squalane | 15.5 |
| (4) polyglyceryl triisostearate | 5.0 |
| (5) volatile fluid isoparaffin | 10.0 |
| (6) ceresin wax | 3.3 |
| (7) candelilla wax | 4.5 |
| (8) colored pigment (Examples 2-2, 3 and 4) | moderate |
| (9) titanium dioxide (Example 2-1) | 15.5 |
| (10) talc (Example 1-3) | 8.0 |
| (11) anti-septics | moderate |
| (12) perfume | moderate |

(Formulating Procedure)

The above ingredients (8) to (10) were mixed and pulverized beforehand. To an oily phase, obtained on mixing and dissolving ingredients (1) to (7) at 85° C. ingredients (8) to (10) pulverized previously, were added and dispersed homogeneously, using a homo-disper. To the resulting mixture was added perfume and the resulting product charged into a metal pan and allowed to cool to produce an oily foundation.

Example 10

Production of a Emulsion

An emulsion having the composition shown in Table 9 was produced by the following method:

TABLE 9

| ingredients | weight parts |
| --- | --- |
| (1) octamethyl cyclotetrasiloxane | 20.0 |
| (2) methylphenyl polysiloxane | 6.0 |
| (3) squalane | 8.5 |
| (4) polyglyceryl diisostearate | 5.0 |
| (5) dimethyl polysiloxane polyoxyalkylene polymer (HLB = 4) | 5.0 |
| (6) butyl paraben | 0.3 |
| (7) talc (Example 1-3) | 1.5 |
| (8) purified water | balance |
| (9) pyrrolidonecarboxylic acid sodium | 2.5 |
| (10) propylene glycol | 5.0 |
| (11) glycerine | 5.0 |
| (12) methyl paraben | 0.2 |
| (13) perfume | moderate |

(Formulating Procedure)

The above ingredients (1) to (6) were mixed and dissolved at 75° C. to give an oily phase to which the ingredient (7) was added and dispersed homogeneously by a homo-dipser. The ingredients (8) to (12) were uniformly mixed and dissolved at 75° C. to give an aqueous phase which then was added gradually to the above-described oily phase and dispersed uniformly by a homo-mixer. The emulsified particles were adjusted in shape and ingredient (13) was added thereto to produce an emulsion.

In the above Example of the present invention, a functional test of the cosmetics was carried out by an expert panel of 20 persons. As the items for evaluation, four test items, smoothness during use, adhesion to the skin, extension on the skin, and natural finish were selected and evaluation was carried out in five stages. Meanwhile, as comparative Examples, methyl hydrogen polysiloxane were coated in the same amounts on the powders for the coated powders incorporated as in Examples 4 and 5 (Comparative Examples 4 and 5), while a 1:1 mixture of octyl trimethoxysilane and trimethylsiloxy silicic acid was coated in the same amount on the powders for the coated powders incorporated as in Examples 6 to 8 (Comparative Examples 6 to 8) and lecithin was coated in the same amount on the powders for the coated powders incorporated as in Examples 9 and 10 (Comparative Examples 9 and 10). The results are shown in Table 10.

(Evaluation Standard)

5: excellent;
4: good;
3: ordinary;
2: slightly poor; and
1: poor.

TABLE 10

| Sample | Smoothness | Adhesion to Skin | Extension on Skin | Natural Finish |
| --- | --- | --- | --- | --- |
| Example 4 | 4.5 | 4.3 | 4.3 | 4.2 |
| Comp. Ex. 4 | 2.1 | 1.9 | 2.0 | 2.3 |
| Example 5 | 4.6 | 4.1 | 4.1 | 4.2 |
| Comp. Ex. 5 | 2.3 | 2.1 | 2.0 | 2.1 |
| Example 6 | 4.2 | 4.3 | 4.5 | 4.6 |
| Comp. Ex. 6 | —* | —* | —* | —* |
| Example 7 | 4.7 | 4.5 | 4.1 | 4.0 |
| Comp. Ex. 7 | 2.8 | 2.9 | 2.7 | 3.2 |
| Example 8 | 4.5 | 4.0 | 4.6 | 4.5 |
| Comp. Ex. 8 | 2.9 | 2.2 | 2.5 | 3.0 |
| Example 9 | 4.4 | 4.2 | 4.5 | 4.8 |
| Comp. Ex. 9 | 3.4 | 3.0 | 3.3 | 2.5 |
| Example 10 | 4.6 | 4.6 | 4.2 | 4.3 |
| Comp. Ex. 10 | 3.5 | 3.2 | 3.5 | 2.9 |

* Molding was not possible.

In the cosmetics containing coated powders of the present invention, functional values of smoothness during use, adhesion to the skin, extension on the skin, natural finish and the like were improved appreciably, as may be seen from Table 10. It is noted that the solid white powders are ordinarily molded using a few percent of the oily agent, whereas, with the coated powders of the present invention, in which the outermost layer of the particle is coated with an oily coating layer, molding is possible without any use of an oily agent.

(Production of Oil Dispersion Paste)

Samples of Example 3-1 and 2 and samples of Comparative Examples 3-1 and 2 were mixed with squalane and passed 3 times through a sand grinder (with a bead diameter of 1 mmφ) for dispersion for preparing a squalane dispersion. The proportions of the powdered samples incorporated in the compositions were adjusted so that the viscosity (25° C.) immediately after preparation of the dispersions at 25° C. as measured by a Vismetron viscometer VDA manufactured by SHIBAURA SYSTEM CO. LTD. was 2000±500 cp. The particle size (D50 and D95) in the dispersions and stability on allowing the dispersions to stand at 50° C. for one month was observed. The compositions of the respective coated powder samples and test results are shown in Table 11.

TABLE 11

| Sample | Powder / Oil weight ratio in Dispersion | Viscosity of Dispersion | Particle Size (μm) D50 | D95 | Stability |
|---|---|---|---|---|---|
| Fine Particulate Titanium dioxide in Example 3-1 | 65 / 35 | 2200 (cpi) | 0.236 | 0.471 | No Separation |
| Fine Particulate Titanium dioxide in Comp. Ex. 3-1 | 35 / 65 | 1800 | 1.353 | 10.540 | Separation |
| Fine Particulate Zinc Oxide in Example 3-1 | 63 / 37 | 1900 | 0.088 | 0.135 | No Separation |
| Fine Particulate Zinc Oxide in Comp. Ex. 3-1 | 38 / 62 | 2300 | 1.269 | 3.099 | Separation |

As may be seen from Table 11, since the oil dispersion paste, containing the coated powder according to the present invention, is superior in affinity and in dispersibility to the oily agent, the proportions of fine particulate titanium dioxide and fine particulate zinc oxide to be incorporated therein can be increased appreciably. It is also possible to maintain this extremely fine particle diameter of the dispersed powder. The dispersion paste, thus obtained, is also superior in stability over an extended period of time.

(Production of UV Shielding Powder Foundation)

A powder foundation of the composition shown in Table 12 was produced by the following method.

TABLE 12

| Ingredients | Example 12-1 | Comp. Ex. 12-1 | Example 12-2 | Comp. Ex. 12-2 |
|---|---|---|---|---|
| (1) Red iron oxide (Example 2-3) | 1.5 | 1.5 | 1.5 | 1.5 |
| (2) Yellow iron oxide (Example 2-2) | 3.0 | 3.0 | 3.0 | 3.0 |
| (3) Black iron oxide (Example 2-4) | 0.1 | 0.1 | 0.1 | 0.1 |
| (4) Titanium dioxide (Example 2-1) | 7.0 | 7.0 | 7.0 | 7.0 |
| (5) Sericite (Example 1-2) | 38.0 | 38.0 | 38.0 | 38.0 |
| (6) Talc (Example 1-3) | Balance | Balance | Balance | Balance |
| (7) Mica (Example 1-1) | 5.0 | 5.0 | 5.0 | 5.0 |
| (8) Fine Particulate Titanium Dioxide | Example 3-1 5.0 | Comp. Ex. 3-1 5.0 | — | — |
| (9) Squalane | 10.0 | 10.0 | 7.3 | 0.7 |
| (10) Oil Dispersion of Fine Particulate Titanium Dioxide | — | — | 7.7*1 | 14.3*2 |
| (11) Dimethyl Polysiloxane | 3.5 | 3.5 | 3.5 | 3.5 |
| (12) Antiseptics | Moderate | Moderate | Moderate | Moderate |
| (13) Perfume | Moderate | Moderate | Moderate | Moderate |

*1 dispersion of the coated powder obtained in Example 3-1.
*2 dispersion of the coated powder obtained in Comparative Example 3-1.

(Formulating Procedure)

The above ingredients (1) to (8) were mixed and passed through a pulverizer. The resulting powdered material was transferred to a high-speed blender and mixed with a uniform mixture of the ingredients (9) to (13). The resulting mixture was further mixed and homogenized. The homogeneous mixture, thus produced, was passed through a pulverizer and sieved to adjust the particle size. The resulting product was compressed and molded to give an UV shielding foundation.

Example 13

(Production of a W/O Sunscreen Cream)

A sunscreen cream, having the composition shown in Table 13, was produced by the following method.

TABLE 13

| ingredients | (Example 13-1) coated powder of Example used | (Comparative Example 13-1) coated powder of Comparative Example used |
|---|---|---|
| (1) volatile fluid isoparaffin | 20.0 | 20.0 |
| (2) vaseline | 2.0 | 2.0 |
| (3) isononyl isononanoate | 6.5 | 6.5 |
| (4) cetanol | 1.0 | 1.0 |
| (5) squalane | 7.09 | — |
| (6) polyethylene glycol monostearate (4EO) | 1.0 | 1.0 |
| (7) hexaglyceryl polyricinoleate | 3.5 | 3.5 |
| (8) dispersion of fine particulate titanium dioxide in squalane* | 4.6 | 8.57 |
| (9) dispersion of fine particulate zinc oxide in squalane* | 4.77 | 7.89 |
| (10) purified water | balance | balance |
| (11) glycerine | 5.0 | 5.0 |
| (12) 1,3-butylene glycol | 5.0 | 5.0 |
| (13) pyrrolidonecarboxylic acid sodium | 2.5 | 2.5 |
| (14) anti-septics | moderate | moderate |
| (15) perfume | moderate | moderate |

*The dispersion of Example 11 was used.

(Formulating Procedure)

The oily ingredients (1) to (9) were dissolved at 75° C. The aqueous ingredients (10) to (14) were dissolved at 75° C., and homogenized. The resulting product was added to the oily ingredients and emulsified by a homo-mixer. Ingredient (15) was added to the resulting emulsion and allowed to cool to produce a sunscreen cream.

In Example 12 of the present invention, measurement of the in-vitro PA value, the in-vitro SPF value (by a SPF analyzer) and stability (allowing to stand at 50° C. for one month) was made. In Example 13, evaluation was made of the transmittance ratio of the visible spectrum, in-vitro PA value, in-vitro SPF value and stability (stability with lapse of time). The results are shown in Table 14.

(Measurement of Transmittance Ratio at the Visible Spectrum)

The sample was coated under the condition of 2 mg/cm$^2$ with a cosmetic sponge on a 4.5 by 4.5 cm surface of a transpore surgical tape manufactured by SUMITOMO 3M INC. At 10 spots on the coating surface, 560 nm transmittance was measured by a spectrophotometer manufactured by SHIMADZU CO. LTD. under the trade name of "UV-160" to obtain a mean value.

(Measurement of in-vitro PA Value and in-vitro SPF Value)

Measurements were made by the SPF analyzer at 12 spots of the sample adjusted by the transmittance ratio of the visible spectrum described above, and mean values were obtained.

TABLE 14

| Sample | Transparency at Visible Spectrum | in-vitro PA Value | in-vitro SPF Value | Preservation Stability of Cream (50° C./1 month) |
|---|---|---|---|---|
| Example 12-1 | — | 7.1 | 10.2 | — |
| Comp. Ex. 12-1 | — | 3.4 | 5.1 | — |
| Example 12-2 | — | 6.3 | 12.0 | — |
| Comp. Ex. 12-2 | — | 3.9 | 5.6 | — |
| Example 13-1 | 60.5 (%) | 23.2 | 25.8 | No Separation |
| Comp. Ex. 13-2 | 25.7 (%) | 6.9 | 13.6 | Slight Separation, Precipitation |

As may be seen from Table 14, the cosmetics admixed with the coated powder according to the present invention are superior in affinity and dispersibility to the oily agent, so that transparency at the visible spectrum and UV light shielding performance at the ultraviolet spectrum of the fine particulate titanium dioxide and fine particulate zinc oxide can be improved significantly. Moreover, the cosmetic, thus produced, is superior in stability.

Example 14

Production of an Emulsion Type Mascara

A mascara of the composition shown in Table 15 was produced by the following method.

TABLE 15

| ingredients | (Example 14) coated power of Example used | (Comparative Example 14) coated powder of Comparative Example used |
|---|---|---|
| (1) vinyl acetate emulsion (50 wt %) | 35.0 | 35.0 |
| (2) carboxymethyl dextran sodium | 1.0 | 1.0 |
| (3) 1,3 butylene glycol | 5.0 | 5.0 |
| (4) keratin hydrolysate | 2.0 | 2.0 |
| (5) anti-septics | moderate | moderate |
| (6) purified water | balance | balance |
| (7) carbon black | 2.0 | 2.0 |
| (8) red iron oxide* | 0.2 | 0.2 |
| (9) titanium dioxide* | 5.0 | 5.0 |

*The powder coated by the method of Example 2-1 was used in Example 14, whilst the powder coated by the method of Comparative Example 2-1 was used in Comparative Example 14.

(Formulating Procedure)

The above ingredients (2) to (5) were mixed into ingredient (6) and dissolved homogeneously beforehand. Next, ingredients (7) to (9) were mixed together and pulverized. Ingredients (7) to (9) were added to ingredient (1) and dispersed therein homogeneously. To this homogeneous dispersion, the previously prepared homogeneous mixture of ingredients (2) to (6) was added and homogeneously dispersed by a homo-mixer to produce an emulsion type mascara.

Example 15

Production of a Nail Enamel

A nail enamel having the composition shown in Table 16 was produced by the following method.

TABLE 16

| ingredients | (Example 15) coated power of Example used | (Comparative Example 15) coated powder of Comparative Example used |
|---|---|---|
| (1) nitrocellulose | 18.0 | 18.0 |
| (2) sucrose benzoate | 6.0 | 6.0 |
| (3) alkyd resin | 7.0 | 7.0 |
| (4) toluenesulfonic acid amide resin | 5.0 | 5.0 |
| (5) camphor | 5.0 | 5.0 |
| (6) ethyl acetate | 22.0 | 22.0 |
| (7) butyl acetate | balance | balance |
| (8) isopropyl alcohol | 6.0 | 6.0 |
| (9) titanium dioxide | 1.5 | 1.5 |
| (10) mica titanium | 0.5 | 0.5 |
| (11) red iron oxide | 0.3 | 0.3 |

(Formulating Procedure)

The above ingredients (5) to (8) were mixed together and admixed with ingredients (1) to (4) to effect uniform dissolution. Further, ingredients (9) to (11) were added thereto and dispersed to produce a nail enamel.

Of the cosmetics obtained in Examples 14 and 15 of the present invention, functional tests were conducted on the optical characteristics (properties) and dispersion stability. An expert panel of twenty persons were also used to conduct tests on feeling and optical properties (glossy look). Functional tests were performed by a five-stage evaluation. The results are shown in Table 17.

(Evaluation Standard)

5: excellent;
4: good;
3: ordinary;
2: slightly poor; and
1: poor.

(Optical Characteristics)

The samples were applied dropwise to a glass plate to form a coating film of 10 µm in thickness, by a doctor blade. Using a variable angle gloss meter, manufactured by NIPPON DENSHOKU INDUSTRIES CO. LTD. under the trade name of "VGS-300A", the gloss values at 20°–20° and 60°–60° were measured.

(Dispersion Stability)

Various samples were preserved for one month in a 48-hour cycle test where the temperature range of from −10° C. to 50° C. to check any possible occurrence of color separation.

TABLE 17

| Sample | 20° −20° Gloss | 60° −60° Gloss | Dispersion Stability (50° C./1 month) | Aesthetic Feel | Glossy look |
|---|---|---|---|---|---|
| Example 14 | 35.3 | 26.8 | No precipitation, No Color Separation | 4.3 | 4.6 |
| Comp. Ex. 14 | 21.2 | 12.7 | Precipitation, Color Separation | 2.8 | 3.0 |
| Example 15 | 68.5 | 56.2 | No Precipitation, No Color Separation | 4.1 | 4.5 |
| Comp. Ex. 15 | 56.8 | 44.7 | Precipitation, Color Separation | 3.4 | 3.1 |

As may be seen from Table 17, the cosmetic containing the coated powder of the present invention is particularly superior in affinity and dispersibility with respect to an oleophilic liquid to enable the function of the powder to be improved appreciably. Moreover, the cosmetic is superior in its performance (feeling) and dispersion stability. In particular, a nail enamel usually contains organic compound-modified clay mineral as to improve the viscosity and stabilize the dispersion. However, with the nail enamel of the present invention, containing the coated powder of the present invention, the formulation can be stabilized sufficiently without using the viscosity improver and the dispersion stabilizer.

Effect of the Invention

As explained particularly in the foregoing, the coated powder, i.e., the surface-treated powder in the present invention is superior in dispersibility, particularly in its affinity to an oleophilic liquid by the coating layer at least containing layers A and B. Moreover, as compared to conventional surface-treated powder, the present powder is drastically improved as to the functions of the powder base which significantly varies with the state of dispersion of the particulate powder particles, such as adhesion to the skin, aesthetic feel (using touch), covering power, coloring power, UV or IR light shielding performance, optical properties and the like. Moreover, a cosmetic of the present invention that contain these excellent powders exhibit superior usability and excellent stability.

The coated powders (surface-treated powders) in the present invention, can be used with powdered materials that are used in the fields other than cosmetics, provided that the powdered materials (substrates) may be usable as cosmetics. Therefore, the coated powders (surface-treated powders) of the present invention can be used equally and conveniently in fields other than cosmetics.

What is claimed is:

1. A surface-treated powder, comprising a powder usable for cosmetics, and coating layers of surface treating agents of a layer A and a layer B, each formed on at least a portion of the powder particle surface, wherein said layer A is a coating layer of a surface treating agent that is a solid at room temperature, said coating layer containing at least one compound selected from the compounds in a reactive organo polysiloxane, a polyolefin, a hydrogenated lecithin or its salt form, an N-acylamino acid or its salt form, a fatty acid or its salt form, and a dextrin fatty acid ester; and wherein said layer B is a coating layer of a surface treating agent that is a liquid at room temperature, said coating layer containing at least one compound selected from the compounds in an organo polysiloxane modified at its sole terminal end with a functional group, an alkylsilane modified at its sole terminal end with a functional group, and a branched fatty acid wherein said layer A is formed on the outermost surface of the particle and said layer B is formed on the outermost surface of layer A.

2. The surface-treated powder as defined in claim 1, wherein said layer A is applied on at least a portion of said particle surface and said layer B is applied further thereon.

3. The surface-treated powder as defined in claim 1, wherein said organo polysiloxane modified at its sole terminal end with a functional group is straight-chained and has a polymerization degree of 10 to 100, said alkylsilane modified at its sole terminal end with a functional group has a 6 to 30 carbon atom alkyl group, and the number of carbon atoms of said branched fatty acid is 8 to 22.

4. The surface-treated powder as defined in any one of claims 1 to 3, wherein the weights of said layers A and B are such that $A \leqq B$.

5. The surface-treated powder as defined in any one of claims 1 to 3, wherein a weight ratio of the powder particle without the layers, to said layer A is 100 to from 0.1 to 10 and wherein that to said layer B is 100 to from 0.1 to 30.

6. The surface-treated powder as defined in any one of claims 1 to 3, wherein said powder has been treated by a jet method.

7. A cosmetic comprising the surface-treated powder as defined in any one of claims 1 to 3.

8. The cosmetic as defined in claim 7, comprising to 100 wt % of said surface-treated powder.

* * * * *